(12) United States Patent
Trujillo-Lemon et al.

(10) Patent No.: US 8,513,326 B2
(45) Date of Patent: Aug. 20, 2013

(54) CARBAMATE-METHACRYLATE MONOMERS AND THEIR USE IN DENTAL APPLICATIONS

(75) Inventors: Marianela Trujillo-Lemon, Parker, CO (US); Kristin Lindsay Wall, Washington, DC (US); Kristina Esquibel, Rifle, CO (US); Jordan Boulden, Thornton, CO (US); Amy J. Docktor, Boulder, CO (US); Zachary R. Shelton, Elizabeth, CO (US); Cora Bracho-Troconis, Superior, CO (US)

(73) Assignee: Septodont Confi-Dental, Louisville, CO (US)

( * ) Notice: Subject to any disclaimer, the term of this patent is extended or adjusted under 35 U.S.C. 154(b) by 457 days.

(21) Appl. No.: 12/756,820

(22) Filed: Apr. 8, 2010

(65) Prior Publication Data

US 2010/0307378 A1 Dec. 9, 2010

Related U.S. Application Data

(63) Continuation-in-part of application No. PCT/US2009/060168, filed on Oct. 9, 2009.

(60) Provisional application No. 61/104,139, filed on Oct. 9, 2008.

(51) Int. Cl.
*A61K 6/08* (2006.01)
*A61K 6/083* (2006.01)
*A61C 5/00* (2006.01)
*C07D 265/00* (2006.01)
*C07D 273/04* (2006.01)

(52) U.S. Cl.
USPC ........ 523/115; 523/116; 523/118; 433/228.1; 106/35; 544/63; 544/67; 544/194

(58) Field of Classification Search
USPC ........ 523/115, 116, 118; 433/228.1; 106/35; 544/63, 67, 194
See application file for complete search history.

(56) References Cited

U.S. PATENT DOCUMENTS

| | | | |
|---|---|---|---|
| 4,279,833 A | 7/1981 | Culbertson et al. | |
| 4,648,843 A * | 3/1987 | Mitra | 433/201.1 |
| 4,813,875 A | 3/1989 | Hare | |
| 4,876,253 A | 10/1989 | Fuhrer et al. | |
| 4,879,402 A | 11/1989 | Reiners et al. | |
| 5,849,270 A * | 12/1998 | Podszun et al. | 424/55 |
| 6,653,375 B2 * | 11/2003 | Moszner et al. | 524/116 |
| 7,078,446 B2 | 7/2006 | Moszner et al. | |

OTHER PUBLICATIONS

Moszner, N.; Völkel, T.; Fischer, U. K.; Klester, A.; Rheinberger, V. Agnew. Makromol. Chem. 1999, 265, 31.*
PCT International Search Report (PCT /US09/60168) dated Feb. 17, 2010.

* cited by examiner

*Primary Examiner* — Michael Pepitone
(74) *Attorney, Agent, or Firm* — Arent Fox LLP

(57) ABSTRACT

The present invention relates, generally, to monomers containing carbamate-methacrylates or derivatives of carbamate-methacrylates, processes for making the monomers, and compositions comprising the monomers. The present invention also relates to methods of using the monomers, such as in dental applications, and in particular, dental restorative resins.

26 Claims, 11 Drawing Sheets

Polymerization Kinetics for new monomers and common dental monomers

Bis-GMA
Chemical Formula: $C_{29}H_{36}O_8$
Molecular Weight: 512.59

EBPADMA
Chemical Formula: $C_{27}H_{32}O_6$

UDMA
Chemical Formula: $C_{23}H_{38}N_2O_8$
Molecular Weight: 470.56

PEM 659

Chemical Formula: $C_{40}H_{50}O_8$
Molecular Weight: 658.82

PEM 665

Chemical Formula: $C_{40}H_{56}O_8$
Molecular Weight: 664.87

TEGDMA

HDDMA

DCP

TMPTMA

DDCDMA

DAOHDMA

DADMA

X-PEM 1058

Figure 9  Conversion values of compositions using new monomers compare with conversion of microhybrid and hybrids commercial products
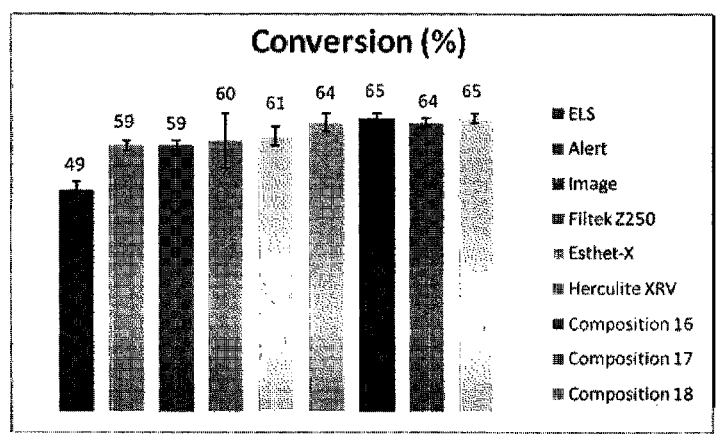

Figure 10  Volume shrinkage values of microhybrid compositions using new monomers comparison with microhybrid and hybrids commercial products
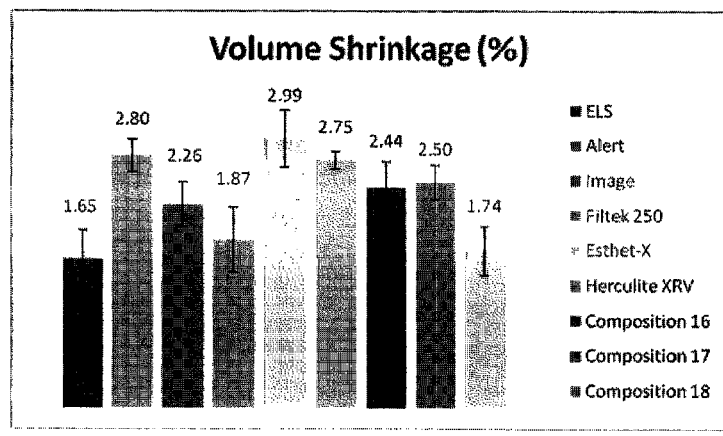

Figure 11 Flexural strength and Young's modulus values of microhybrid compositions using new monomers compare with those of microhybrid and hybrids commercial products
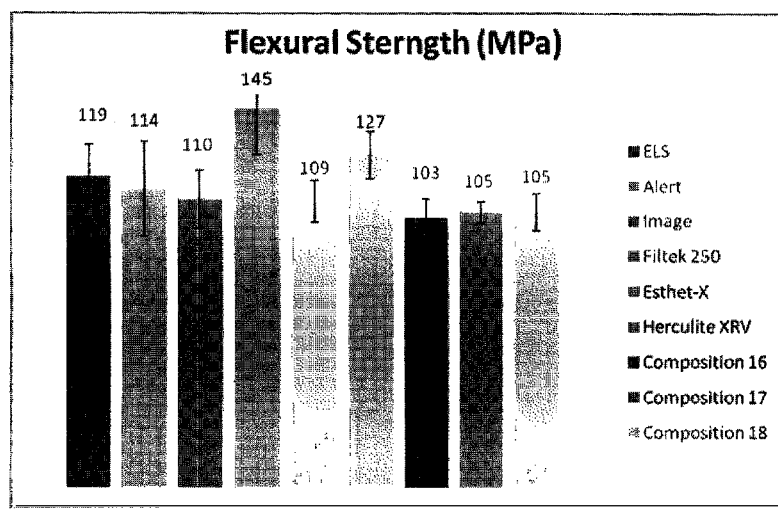
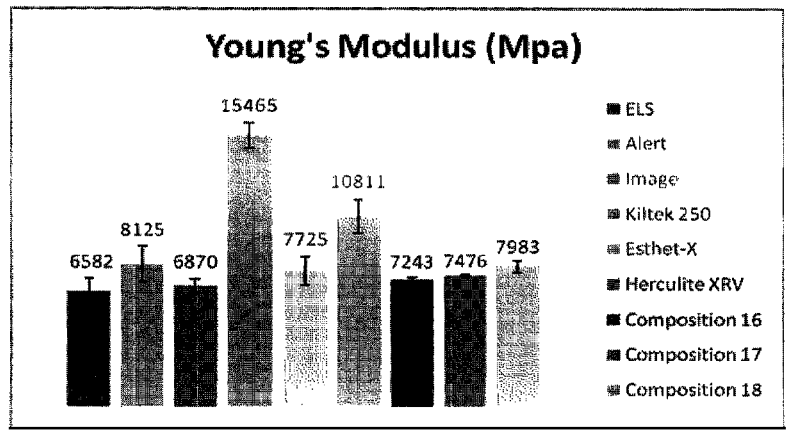

CARBAMATE-METHACRYLATE MONOMERS AND THEIR USE IN DENTAL APPLICATIONS

CROSS-REFERENCE TO RELATED APPLICATION

This application is a continuation-in-part application of International Application No. PCT/US2009/060168, having international filing date of Oct. 9, 2009, which claims International priority to Provisional Patent Application No. 61/104,139, filed Oct. 9, 2008, the disclosure of each of which is hereby incorporated in its entirety by reference.

FIELD OF THE INVENTION

The present invention relates, generally, to monomers containing carbamate-methacrylates or derivatives of carbamate-methacrylates, processes for making the monomers, and compositions comprising the monomers. The carbamate-methacrylates are preferably aromatic, and the aromatic functionality is preferably incorporated by reaction of isocyanate and aromatic polymerizable alcohols. The present invention also relates to methods of using the monomers, such as in dental applications, and in particular, dental restorative resins.

BACKGROUND OF THE INVENTION

Compositions for dental applications generally consist of methacrylic-type monomers which react "on-command" through a chain-growth, free radical polymerization mechanism. Known dimethacrylate systems in the art are popular for dental fillings and other dental prostheses due to their unique combination of properties, such as fast free radical polymerization, good mechanical properties and an aesthetic appearance. Commonly used acrylic monomers in the dental field are generally linear aliphatic or partially aromatic core groups with a terminal methacrylate functionality, such as 2,2-bis[p-(2'-hydroxy-3'-methacryloxypropoxy)phenyl]-propane (commonly referred as BisGMA) and urethane dimethacrylate (commonly referred as UDMA), as shown in FIG. 1.

In the field of dental materials, carbamate (or urethane) methacrylate derivatives have been widely described and used as monomers for dental applications. For example, UDMA synthesized by reaction of 2,2,4-trimethylhexamethylene diisocyanate with 2-hydroxyethyl methacrylate (HEMA) has found practical applications as a constituent of dental adhesives and dental composites materials. However, the refractive index of UDMA ($\eta_D$=1.483) is lower than dental filling materials ($\eta_D$=1.52-1.56), so UDMA and others known in the art aliphatic urethanes (for example the ones describe in U.S. Pat. No. 4,813,875, U.S. Pat. No. 4,879,402 and U.S. Pat. No. 7,078,446) have to be used in combination with a high refractive index monomer, like bisphenol-A-diglycidyl methacrylate (Bis-GMA) to provide not just increase in refractive indices but also to increase the mechanical properties of the final dental compositions.

Even though, UDMA in combination with Bis-GMA are present in a wide range of commercial dental restorative materials, the use of such monomers are not without disadvantages. They are generally extremely viscous monomers and are typically diluted with low viscosity methacrylic monomers, such as triethyleneglycoldimethacrylate (TEGDMA), among others (FIG. 2).

Furthermore these monomers and their polymers have several critical deficiencies that limit their clinical performance in dental restorative compositions. For example, existing monomers present relatively low conversion, excessive polymerization shrinkage, poor toughness and excessive water uptake, which are undesirable properties. Known systems often can only reach a final double bond conversion of 55 to 65 percent, which not only contributes to insufficient mechanical properties and wear resistance, but also jeopardizes the biocompatibility of the materials due to leachable, unreacted monomers. As mentioned briefly above, existing dimethacrylate monomers often exhibit significant volumetric shrinkage during polymerization and the induced shrinkage stress results in tooth-composite adhesive failure, initiating microleakage and current caries, which can significantly reduce the longevity and utility of the dental restorative composite. Attempts to increase the final double bond conversion to reduce the unreacted monomers unfortunately lead to an increase in volumetric shrinkage and shrinkage stress.

Several approaches to increase conversion and reduce curing shrinkage have been reported. The amount of shrinkage can be reduced to some extent by increasing filler content. However, when the filler content is too high, it is sometimes difficult to mix the fillers with organic resins. Chemical approaches to increasing conversion and reducing curing shrinkage have been mainly focused on the development of new monomers. One alternative which addresses the shortcomings present in common resins is the use of methacrylate derivatives with high molecular weights. However, typically, the synthesis of these monomers often requires several reaction and purification steps and/or occurs at high temperatures or the synthesized materials are crystalline products which is detrimental for shelf life of the materials due to the risk of precipitation of the solid monomers in the dental compositions with the time. In the other hand, media reports about the possible harmful effects of bisphenol-A (BPA) derivatives have created public concern regarding the presence of Bis-GMA as component in dental materials. Therefore, there is an unmet need in the art for monomers capable of flowing and capable of undergo polymerization that can be produced in a relatively minimal number of steps and which can provide reduced potential for toxicity, reduced polymerization shrinkage, and increased conversion.

The present invention meets the unmet needs of the art by providing viscous liquids which are not bisphenol A-based, and which are high conversion, low volume shrinkage multi-functional carbamate-methacrylate derivatives with refractive indices that match those of dental fillers and have mechanical properties that can be tailored according to the final dental application.

DESCRIPTION OF THE RELATED ART

U.S. Pat. No. 3,425,988 discloses polymerizable polyacrylate sealant compositions containing an acrylate terminated monomer and a peroxy polymerization initiator.

U.S. Pat. No. 4,383,826 discloses polymerizable adducts of diisocyanates and methacryloyl alkyl ethers, alkoxybenzenes, and alkoxycycloalkanes. U.S. Pat. No. 4,383,826 discloses the use of these compounds in compositions for bone cement, fillings for cavities, and orthodontic adhesives.

U.S. Pat. No. 6,653,375 discloses urethane di(meth)acrylate derivatives of 1-3-bis(1-isocyanato-1-methylethyl)benzene and the use of these derivatives in dental materials.

U.S. Pat. No. 4,362,888 discloses polymerizable dimethyacrylate compounds which can be used in compositions for dental applications, and a method of polymerizing the compounds in situ on the teeth.

U.S. Patent Application Publication No. 2005/0267254 discloses functionalized urethane compounds that are useful as thermosetting resins for the electronics packaging industry. U.S. Patent Application Publication No. 2005/0267254 discloses that the compounds can be prepared by contacting a hydroxyl-bearing compound with an isocyanate.

PCT International Publication WO 2005/107626 discloses dimer acid-derived dimethacrylates and polymer systems for use as dental restorative resins.

Atai et al., "Synthesis, characterization, shrinkage and curing kinetics of a new low-shrinkage urethane dimethacrylate monomer for dental applications," *Dental Materials,* 23 (2007): pp. 1030-1041, discloses isophorone-based urethane dimethacrylate (IP-UDMA) resin monomers. Atai et al. discloses that the monomer is synthesized through a reaction of polyethylene glycol 400 and isophorone diisocyanate, followed by a reaction with 2-hydroxyethyl methacrylate (HEMA) to terminate it with methacrylate end groups.

Buruiana et al., "Synthesis of oligomeric urethane dimethacrylates with carboxylic groups and their testing in dental composites," *J Polymer Science: Part A: Polymer Chemistry,* 45 (2007): pp. 1956-1967, discloses carboxyl urethane dimethacrylate oligomers with poly(ethylene oxide) sequences in the structure, and their use in dental materials.

Moszner et al., "A partially aromatic urethane dimethacrylate as a new substitute for Bis-GMA in restorative composites," *Dental Materials,* 24 (2008): pp. 694-699, discloses partially aromatic urethane dimethacrylates in visible-light cured resin-based composite dental restoratives. Moszner et al. discloses the use of the dimethacrylates as a substitute for Bis-GMA.

Mitra S., "Dental composites prepared from resin matrices containing ethylenically unsaturated carbamoyl isocyanurates," *Polymer Preprints,* 1997, 38(2): pp. 103-4, discloses methacrylate functionalized polymerizable compounds. Mitra also discloses resin matrix materials for composites in which the isocyanurate ring serves as a focal point for obtaining a cross-linked resin network.

PCT International Publication WO 2009/042574 discloses methacrylate based monomers containing a urethane linkage, process for production and uses. The methacrylate-urethane monomers described in WO 2009/042574 this invention are preferably based on bisphenol cores including Bisphenol F, Bisphenol A, Bisphenol AP.

All references cited herein are incorporated by reference in their entirety.

SUMMARY OF THE INVENTION

There is an unmet need for flowable monomers that can be produced in a relatively minimal number of steps and which can have reduced potential for toxicity, reduced polymerization shrinkage, and increased conversion.

The present invention provides for viscous, high conversion, low volume shrinkage monomers that are preferably not bisphenol-A-based, which contain carbamate-methacrylates or derivatives of carbamate-methacrylates, and compositions comprising such monomers. The carbamate-methacrylates are preferably aromatic, and the aromatic functionality is preferably incorporated by reaction of isocyanate and aromatic polymerizable alcohols. The monomers of the present invention preferably have refractive indices which match those of dental fillers and have mechanical properties that can be tailored according to the final dental application.

The present invention also provides for methods of producing monomers containing carbamate-methacrylates or derivatives of carbamate-methacrylates.

The present invention also provides for methods of using monomers containing carbamate-methacrylates or derivatives of carbamate-methacrylates in dental applications.

DETAILED DESCRIPTION OF THE INVENTION

The present invention relates to monomers having formula (I):

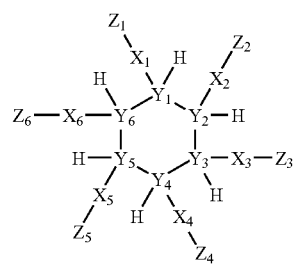

wherein:
the ring structure of formula (I) is saturated or contains up to three unsaturations;

$Y_1$-$Y_6$, each independent from each other, is selected from the group consisting of: C, O, N, and S, wherein at least one of $Y_1$-$Y_6$ is O, N, or S, with the proviso that preferably at least two of $Y_1$-$Y_6$ is C, and wherein:

(i) when any one of $Y_1$-$Y_6$ is O, S, or an unsaturated nitrogen, then the corresponding H, $X_1$-$X_6$ and $Z_1$-$Z_6$ are absent, and (ii) when any one of $Y_1$-$Y_6$ is a saturated nitrogen or an unsaturated carbon, then the corresponding H is absent $X_1$-$X_6$, each independent from each other, is a direct bond, or is selected from the group consisting of: =O, =S, and $R_x$, wherein $R_x$ is a $C_1$-$C_{10}$ group optionally having at least one unsaturation, branch and/or cycle, which is substituted up to 4 times or unsubstituted, and which may be interrupted by at least one O or S, wherein the substituents are each independently selected from the group consisting of —OH, —OR, =O, =S, —O$_2$CR, —SH, —SR, —SOCR, —NH$_2$, —NHR, —N(R)$_2$, —NHCOR, —NRCOR, —I, —Br, —Cl, —F, —ON, —CO$_2$H, —CO$_2$R, —CHO, —COR, —CONH$_2$, —CONHR, —CON(R)$_2$, —COSH, —COSR, —NO$_2$, —SO$_3$H, —SOR, and —SO$_2$R, wherein R is a linear, branched or cyclic alkyl of one to ten carbon atoms, $Z_1$-$Z_6$, each independent from each other, is selected from the group consisting of:

(a) H;
(b) a radical of formula (II):

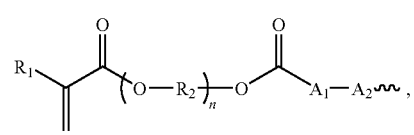

wherein:
$R_1$ is selected from the group consisting of: H and $R_x$, as described above, $R_2$ is $R_x$, as described above;
n is an integer from 1 to 10,
$A_1$ is a direct bond or $R_x$, as described above; and
$A_2$ is selected from the group consisting of O and NH;
(c) a radical of formula (V):

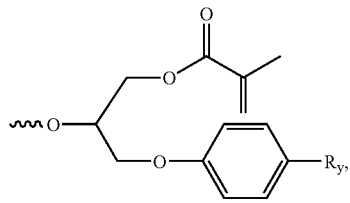

(V)

wherein $R_y$ is selected from the group consisting of H, $CH_3$, $CH_2CH_3$, $C(CH_3)_3$, OH, COOH, anhydride, $O=P(OH)_2$, and $=P(CH_2)_m(OH)_2$, and wherein m=1 to 4; and
(d) a radical of formula (VI):

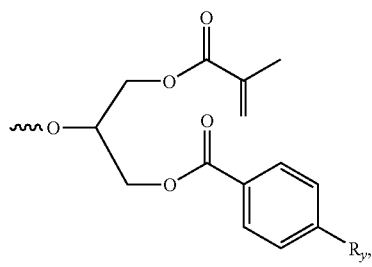

(VI)

wherein $R_y$ is as described above;

with the proviso that at least one, preferably at least two, most preferably at least three, of $Z_1$-$Z_6$ is independently a radical of formula (II), (V) or (VI), and wherein when any one of $X_1$, $X_2$, $X_3$, $X_4$, $X_5$, or $X_6$ is H, =O, or =S, then the respective $Z_1$, $Z_2$, $Z_3$, $Z_4$, $Z_5$, or $Z_6$ is absent.

In preferred embodiments of the invention, at least two, and more preferably, three, of $Y_1$-$Y_6$ are O, N, or S. In preferred embodiments, at least two, and preferably at least three of $Y_1$-$Y_6$ is C. In preferred embodiments, at least two, and more preferably, three, of $Y_1$-$Y_6$ are N.

In preferred embodiments, at least one, and more preferably, two, of $X_1$-$X_6$ are =O or =S. In preferred embodiments, at least one of $X_1$-$X_6$ is $R_x$.

In preferred embodiments, one or more of $Z_1$-$Z_6$ is the following:

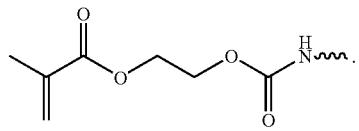

In preferred embodiments, in formula (II), $R_1$ is a $CH_3$.
In preferred embodiments, in formula (II), $R_2$ is a $C_2$ alkyl.
In preferred embodiments, in formula (II), n is 1.
In preferred embodiments, in formula (II), $A_1$ is a direct bond.
In preferred embodiments, in formula (II), $A_2$ is NH.

The present invention also relates to a compound of formula (Ia):

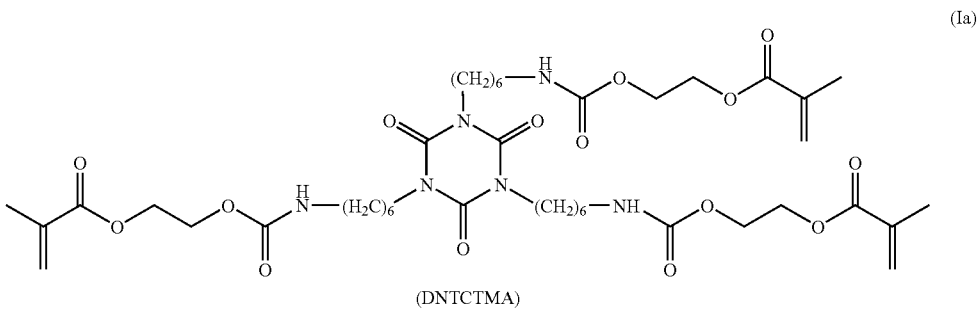

(Ia)

(DNTCTMA)

The present invention also relates to a compound of formula (Ib):

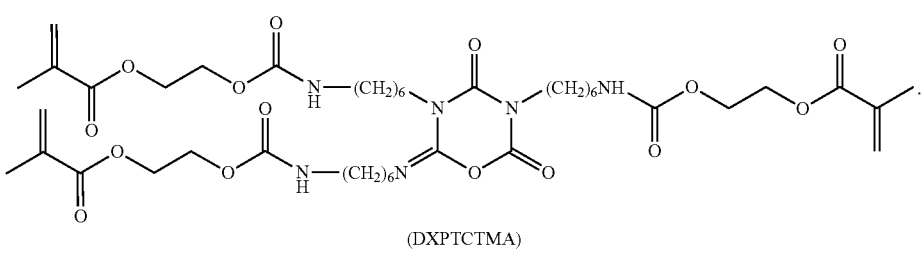

(Ib)

(DXPTCTMA)

The present invention also relates to a compound of formula (Ic):
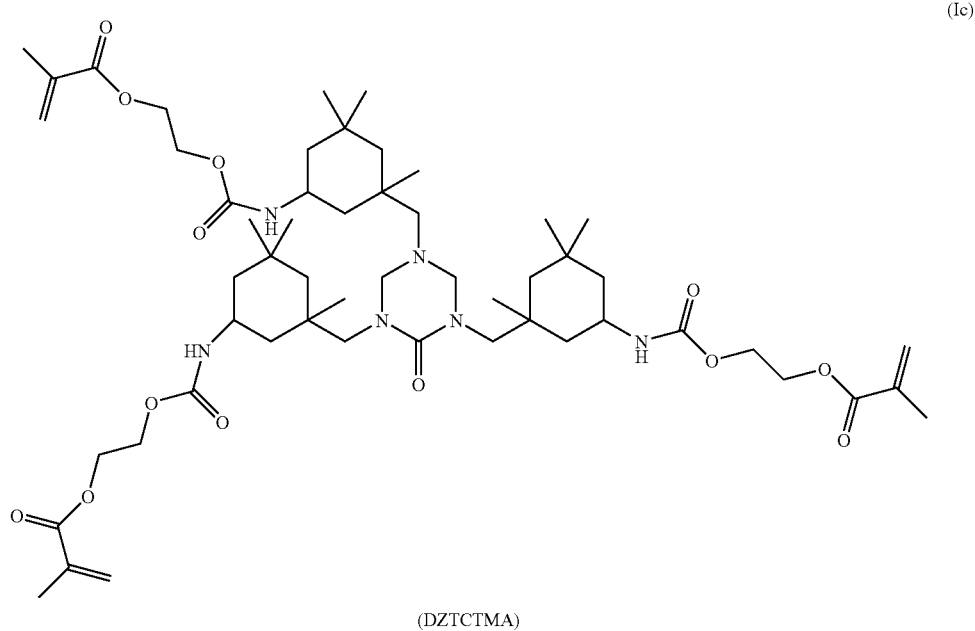 [SMILES: C=C(C)C(=O)OCCOC(=O)NC1CC(C)(C)CC(C)(CN2CN(CC3(C)CC(NC(=O)OCCOC(=O)C(=C)C)CC(C)(C)C3)C(=O)N(CC3(C)CC(NC(=O)OCCOC(=O)C(=C)C)CC(C)(C)C3)C2)C1]
(DZTCTMA)
The present invention also relates to a compound of formula (Id):
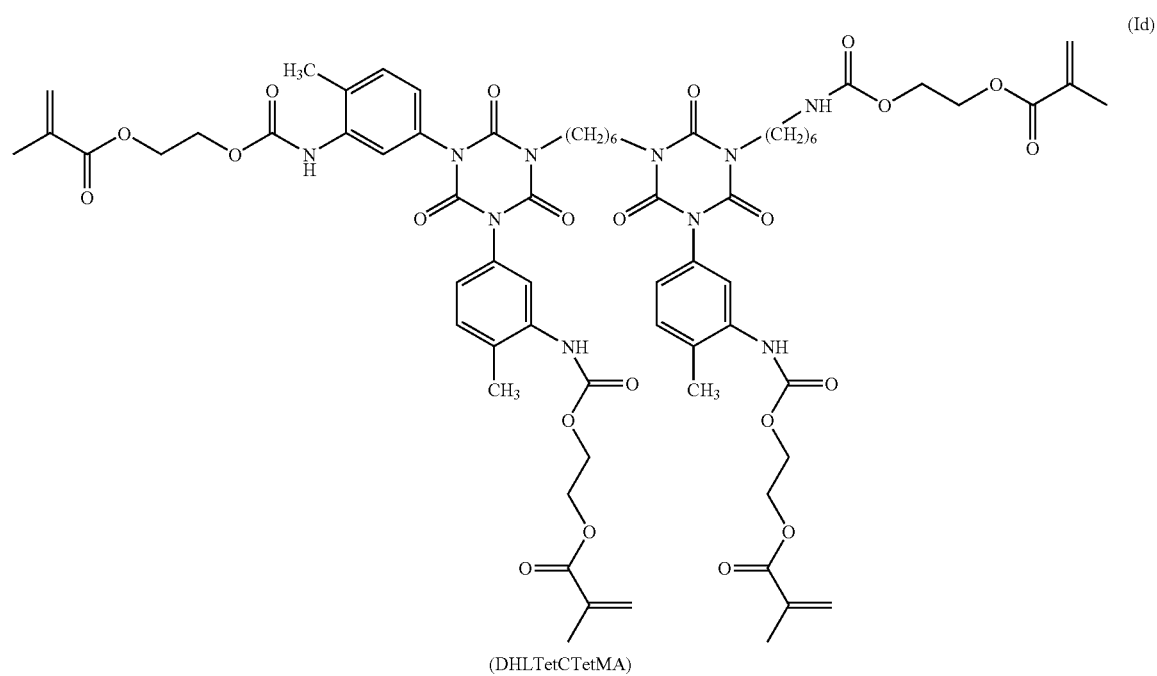
(DHLTetCTetMA)

The present invention also relates to a compound of formula (III)

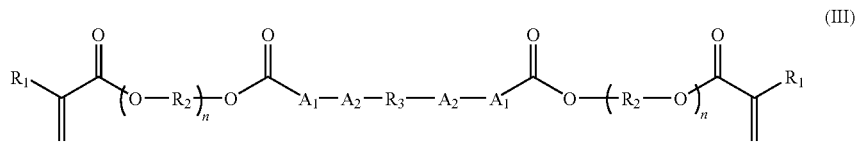

wherein:

$R_1$ is as described above, $R_2$ is $C_1$-$C_{25}$, preferably $C_2$ to $C_{18}$, more preferably $C_2$ to $C_4$ or $C_9$ to $C_{17}$, group, optionally having at least one unsaturation, branch and/or cycle, which is substituted up to 4 times or unsubstituted, and which may be interrupted by at least one O or S, wherein the substituents are each independently selected from the group consisting of —OH, —OR, =O, =S, —O$_2$CR, —SH, —SR, —SOCR, —NH$_2$, —NHR, —N(R)$_2$, —NHCOR, —NRCOR, —I, —Br, —Cl, —F, —CN, —CO$_2$H, —CO$_2$R, —CHO, —COR, —CONH$_2$, —CONHR, —CON(R)$_2$, —COSH, —COSR, —NO$_2$, —SO$_3$H, —SOR, and —SO$_2$R, wherein R is a linear, branched or cyclic alkyl of one to ten carbon atoms, $R_3$ is a $C_6$-$C_{50}$, preferably $C_6$ to $O_{25}$, more preferably $C_6$ to $O_{15}$, group optionally having at least one unsaturation, branch or cycle, which is substituted up to 4 times or unsubstituted and which may be interrupted by at least one O or S, wherein the substituents are each independently selected from the group consisting of —OH, —OR, =O, =S, —O$_2$CR, —SH, —SR, —SOCR, —NH$_2$, —NHR, —N(R)$_2$, —NHCOR, —NRCOR, —I, —Br, —Cl, —F, —CN, —CO$_2$H, —CO$_2$R, —CHO, —COR, —CONH$_2$, —CONHR, —CON(R)$_2$, —COSH, —COSR, —NO$_2$, —SO$_3$H, —SOR, and —SO$_2$R, wherein R is as described above; and n, $A_1$, and $A_2$ are as described above.

In preferred embodiments, in formula (III), $R_1$ is a $CH_3$.

In preferred embodiments, in formula (III), $R_2$ is a $O_2$ alkyl or is selected from the group consisting of:

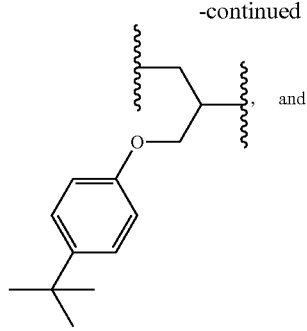

-continued

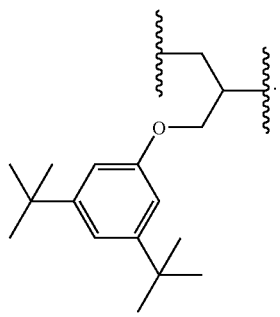

In preferred embodiments, in formula (III), n is 1.

In preferred embodiments, in formula (III), $A_1$ is a direct bond.

In preferred embodiments, in formula (III), $A_2$ is NH.

The present invention also relates to the compound of formula (IIIa):

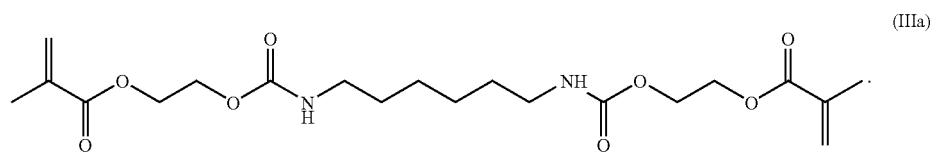 [SMILES: C=C(C)C(=O)OCCOC(=O)NCCCCCCNC(=O)OCCOC(=O)C(=C)C]

The present invention also relates to the compound of formula (IIIb)
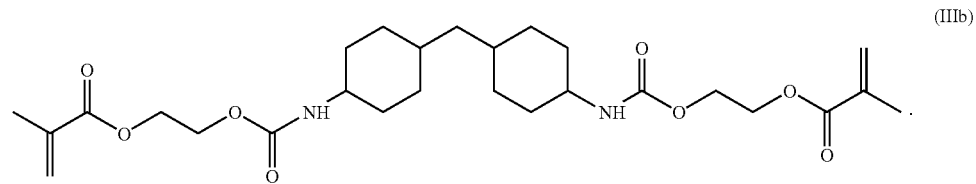 [SMILES: C=C(C)C(=O)OCCOC(=O)NC1CCC(CC2CCC(NC(=O)OCCOC(=O)C(=C)C)CC2)CC1]
The present invention also relates to the compound of formula (IIIc):
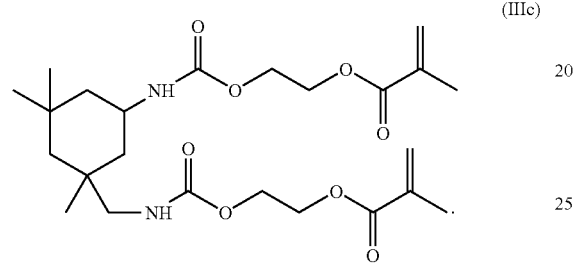
The present invention also relates to the compound of formula (IIId):
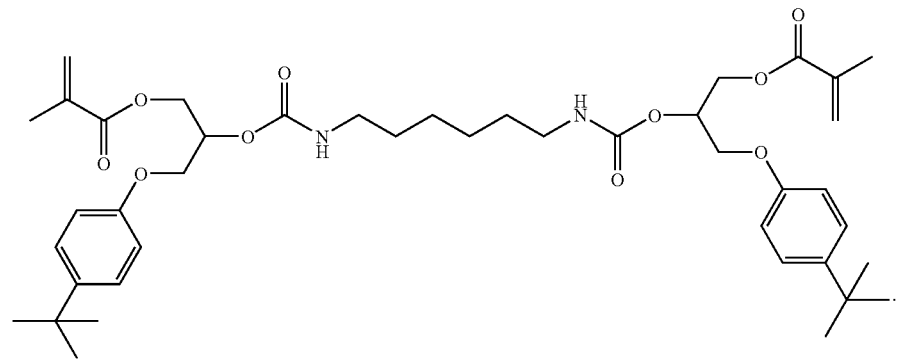
The present invention also relates to the compound of formula (IIIe):
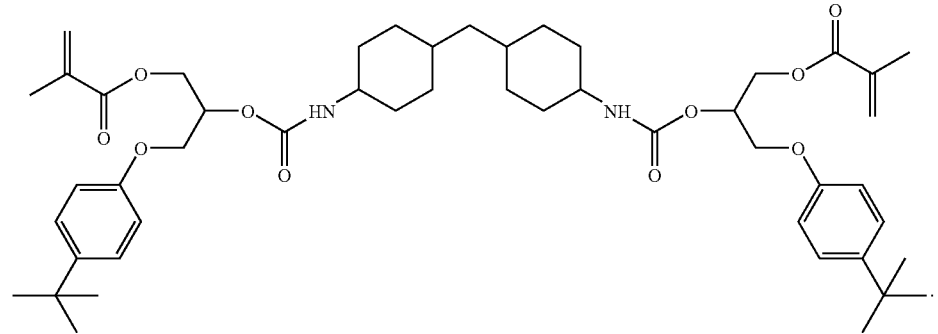

The present invention also relates to the compound of formula (IIIf):
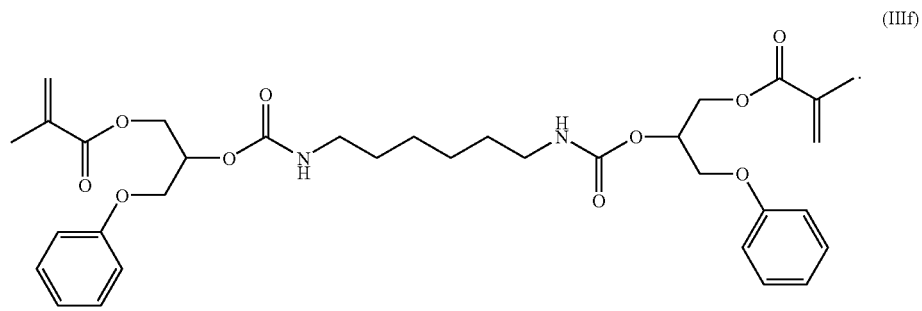 [SMILES: C=C(C)C(=O)OCC(COc1ccccc1)OC(=O)NCCCCCCNC(=O)OC(COC(=O)C(=C)C)COc1ccccc1]
The present invention also relates to the compound of formula (IIIg):
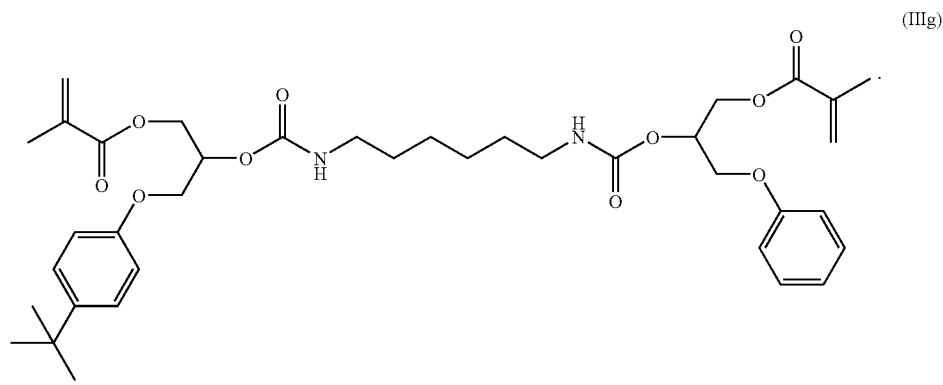 [SMILES: C=C(C)C(=O)OCC(COc1ccccc1)OC(=O)NCCCCCCNC(=O)OC(COC(=O)C(=C)C)COc1ccc(C(C)(C)C)cc1]
The present invention also relates to the compound of formula (IIIh):
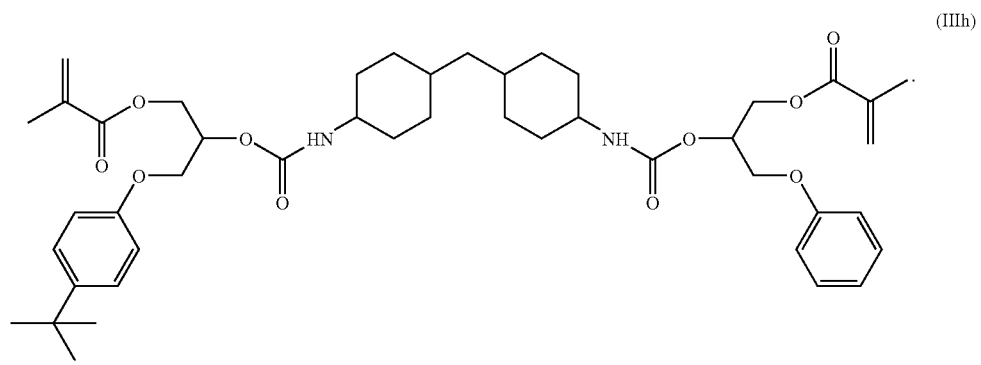 [SMILES: C=C(C)C(=O)OCC(COc1ccccc1)OC(=O)NC1CCC(CC2CCC(NC(=O)OC(COC(=O)C(=C)C)COc3ccc(C(C)(C)C)cc3)CC2)CC1]

The present invention also relates to the compound of formula (IIIi):
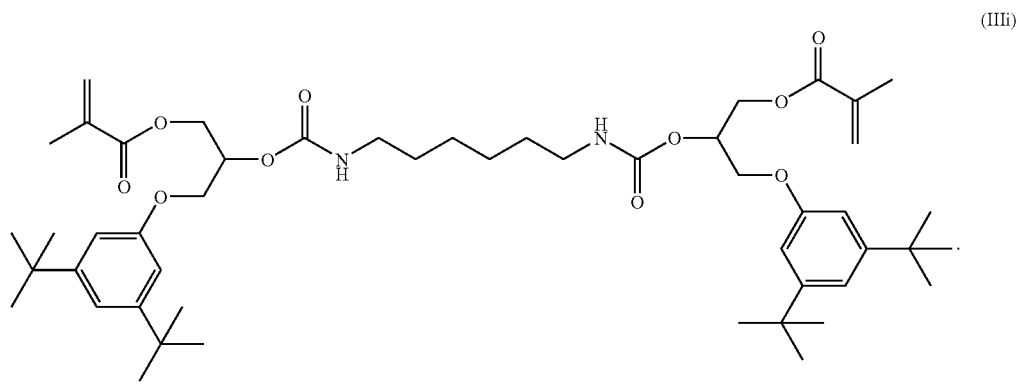 [SMILES: C=C(C)C(=O)OCC(COc1cc(C(C)(C)C)cc(C(C)(C)C)c1)OC(=O)NCCCCCCNC(=O)OC(COC(=O)C(=C)C)COc1cc(C(C)(C)C)cc(C(C)(C)C)c1]
The present invention also relates to the compound of formula (IIIj):
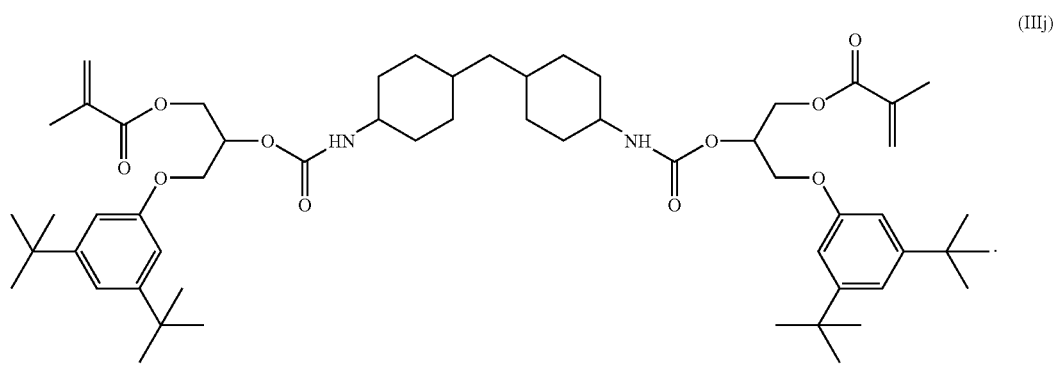 [SMILES: C=C(C)C(=O)OCC(COc1cc(C(C)(C)C)cc(C(C)(C)C)c1)OC(=O)NC1CCC(CC2CCC(NC(=O)OC(COC(=O)C(=C)C)COc3cc(C(C)(C)C)cc(C(C)(C)C)c3)CC2)CC1]
The present invention also relates to the compound of formula (IIIk):
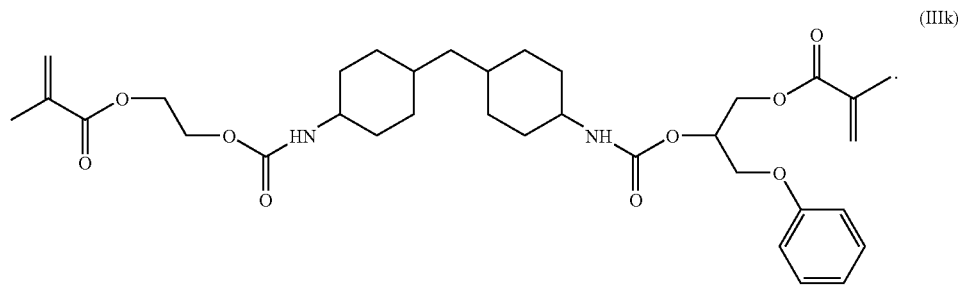 [SMILES: C=C(C)C(=O)OCCOC(=O)NC1CCC(CC2CCC(NC(=O)OC(COC(=O)C(=C)C)COc3ccccc3)CC2)CC1]

The present invention also relates to the compound of formula (IIIL):

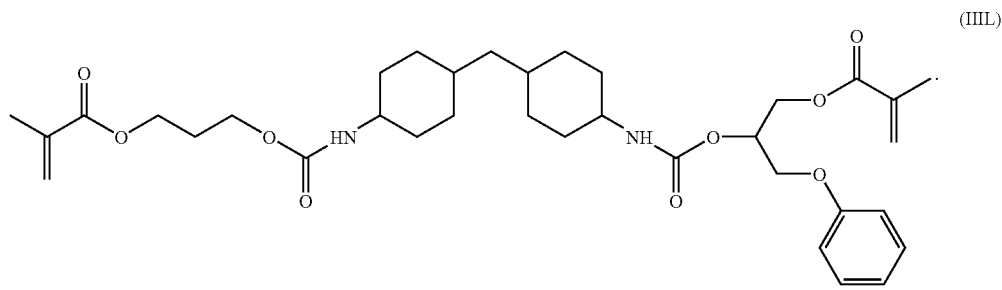 [SMILES: C=C(C)C(=O)OCCCOC(=O)NC1CCC(CC2CCC(NC(=O)OC(COC(=O)C(=C)C)COc3ccccc3)CC2)CC1]
(IIIL)

The present invention also relates to the compound of formula (IIIm):

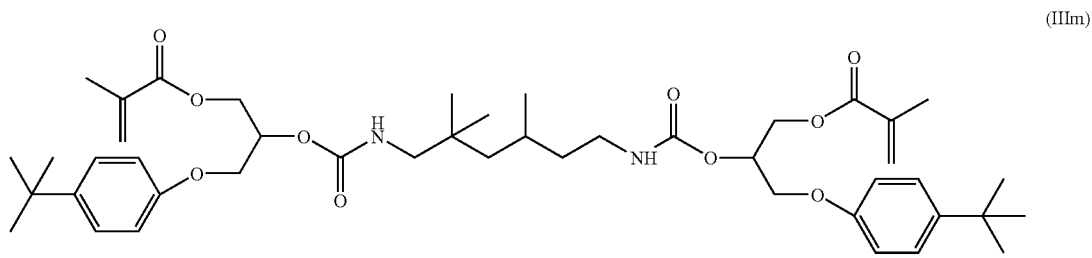 [SMILES: C=C(C)C(=O)OCC(COc1ccc(C(C)(C)C)cc1)OC(=O)NCCC(C)CC(C)(C)CNC(=O)OC(COC(=O)C(=C)C)COc1ccc(C(C)(C)C)cc1]
(IIIm)

The present invention also relates to the compound of formula (IIIn):

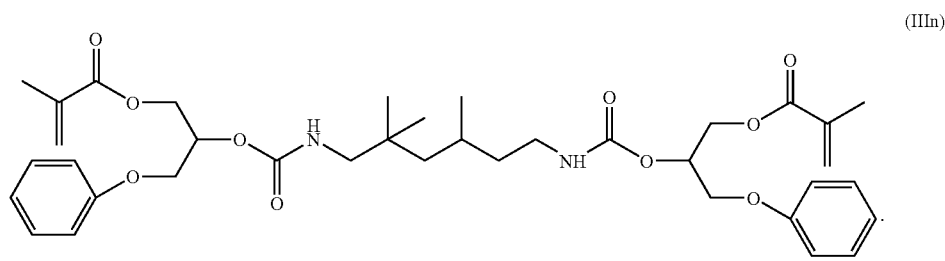 [SMILES: C=C(C)C(=O)OCC(COc1ccccc1)OC(=O)NCCC(C)CC(C)(C)CNC(=O)OC(COC(=O)C(=C)C)COc1ccccc1]
(IIIn)

The present invention also relates to the compound of formula (IIIo):

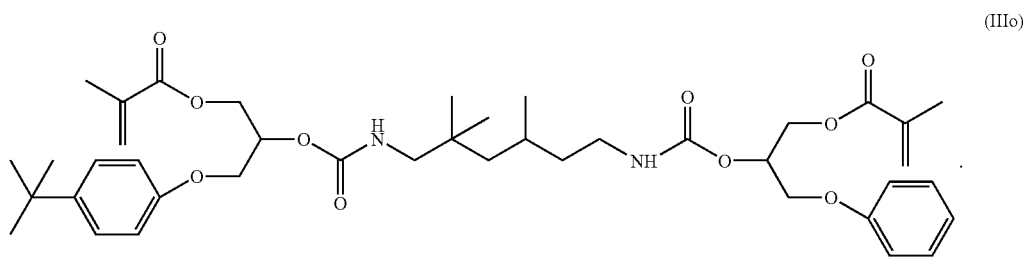 [SMILES: C=C(C)C(=O)OCC(COc1ccccc1)OC(=O)NCCC(C)CC(C)(C)CNC(=O)OC(COC(=O)C(=C)C)COc1ccc(C(C)(C)C)cc1 ; "."]
(IIIo)

Without being bound by theory, the bulky nature of the compounds appears to allow for lower polymerization shrinkage, in addition to an increase of conversion, due to significant flexibility and reduced crosslink density.

It is known in the art that volume shrinkage is typically influenced by two different effects: the replacement of the Van der Waals distance of the monomers by covalent bonds during polymerization, and the packing density of monomers.

Compared with commercially available dental monomers, some of the monomers of the present invention have higher molecular volume and a number of functionalities (double bonds), which can lead to a less tightly packed polymer network after polymerization, resulting in smaller density differences between monomers and polymers and, consequently, smaller volume shrinkage, which translates into maintained or improved durability of the dental materials containing the compositions.

Certain monomers or mixtures of monomers in the present invention show refractive indices (e.g. $\eta_D$=1.51 to 1.53) which match those of the dental fillers, Refractive index matching between the monomers and the fillers allowed for more light transmittance through the composite dental materials, which results in increasing depth of cure, which is important for the assessment of the clinical performance of the composite, as well as aesthetics of the materials through the improvement of the composite shade matching.

Preferred embodiments of the monomers of the present invention have improved biocompatibility compared to compounds such as BisGMA and EBPADMA.

The present invention also relates to process for making the compounds described above.

The present invention relates to a process of producing the compound of formula (I), comprising reacting:

1) a compound of formula (Is):

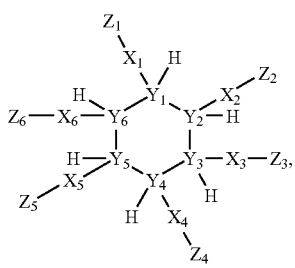

(Is)

wherein $Y_1$-$Y_6$ are as defined for formula (I);

wherein $X_1$-$X_6$ are as defined for formula (I); and and wherein $Z_7$-$Z_{12}$, independent from each other, are selected from the group consisting of H, —N=C=O, and —COOH, with the proviso that at least one of $Z_7$-$Z_{12}$ is —N=C=O or —COOH; and wherein when any one of $X_1$-$X_6$ is H, =O, or =S, then the respective $Z_7$-$Z_{12}$ is absent; with (2) a compound selected from the group consisting of:
  (a) a compound of formula (IV):

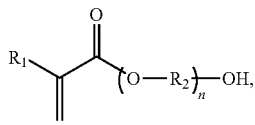

(IV)

wherein $R_1$, $R_2$ and n are as defined for formula (II);

b) a compound of formula ($V_S$):

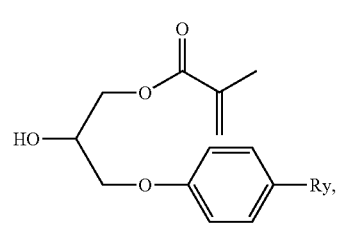

($V_s$)

wherein $R_y$ is as defined in formula (V); and
  c) a compound of formula ($VI_s$):

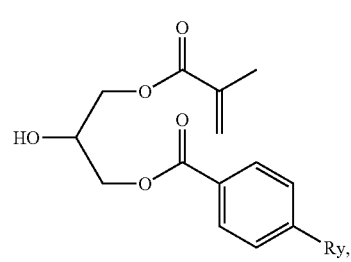

($VI_s$)

wherein $R_y$ is as defined in formula (VI).

The present invention also relates to a process of producing the compound of formula (III), comprising reacting:

(1) a compound selected from the group consisting of:
  (a) a compound of formula (IIIs):

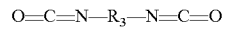

O=C=N—$R_3$—N=C=O  (IIIs)

wherein $R_3$ is as defined for formula (III), and
  (b) a compound of formula (IIIt):

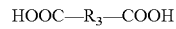

HOOC—$R_3$—COOH  (IIIt)

wherein $R_3$ is as defined for formula (III);
with
(2) a compound of formula (IV):

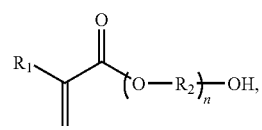

(IV)

wherein $R_1$, $R_2$ and n are as defined for formula (III).

In some embodiments, the compound of formula (IV) is hydroxyethyl methacrylate (HEMA):

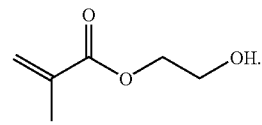

In preferred embodiment, the processes for producing the compound of formula (I) and the compound of formula (III), further comprises using one or more catalysts, preferably catalysts selected from the group consisting of: tertiary amines, organometallic compounds, and inorganic compounds. In preferred embodiments, the organometallic compounds are selected from the group consisting of dibutyl tin dilaurate (DBTDL), dioctyl tin dilaurate (DOTDL), and the inorganic compound is zirconium acetylacetonate. In more preferred embodiments, the catalyst is dibutyl tin dilaurate (DBTDL).

In some embodiments of the present invention, the processes for producing the compound of formula (I) and the compound of formula (III), further comprises using one or more stabilizers. In preferred embodiments, the stabilizer is selected from the group consisting of: a hydroquinone, a p-benzoquinone, and a p-butyl-hydroxytoluene. In more preferred embodiments, the stabilizer is hydroquinone monomethylether (MEHQ) or 2,6-di-tert-butyl-p-cresol (BHT).

In preferred embodiments of the present invention, the processes for producing the compound of formula (I) and the compound of formula (III), occur at a temperature of about 0 to 100° C., more preferably 0 to 80° C., and most preferably 20 to 50° C.

In preferred embodiments of the present invention, the processes for producing the compound of formula (I) and the compound of formula (III), occurs over a time period of between about 1 minute and about 5 days, more preferably between about 12 to 60 hours, and most preferably between about 18 to about 48 hours.

The present invention also relates to compositions comprising the compounds of formula (I) or compounds of formula (III). The present invention also relates to compositions comprising one or more of the compounds of formula (IIIa), (IIIb), (IIIc), (Ia), (Ib), (Ic), or (Id).

In some embodiments, the compositions further comprise one or more monomers, such as high molecular weight monomers, which can aid in reducing volume shrinkage. In preferred embodiments, the compositions further comprise one of more diluent monomers, which can be used to decrease the viscosity of the compositions. Examples of comonomers that may be present in the composition include, but are not limited to: hydrophobic, low viscosity monomers such as EBPADMA, UDMA, DDCDMA, DAOHDMA, 1,6 hexanediol dimethacrylate (HDDMA), 1,4 butanediol dimethacrylate, 1,9 nonanediol dimethacrylate, undecyl methacrylate, lauryl methacrylate, norbornyl methacrylate, isobornyl methacrylate, and n-octyl methacrylate. The comonomer preferably comprises at least one functional group which produces phase-separated polymer upon polymerization. In some embodiments, phase separation during polymerization accounts for low shrinkage and reduced stress despite high levels of conversion.

In preferred embodiments, the compositions further comprise one or more filler materials or compounds. The composition may contain any filler material suitable for use in dental applications, including, but not limited to silanized inorganic compounds. Filler materials include, but are not limited to, compounds which can increase viscosity and increase strength.

In preferred embodiments, the compositions can comprise filler materials selected from the group consisting of: silica, silicate glass, quartz, barium silicate, strontium silicate, barium borosilicate, strontium borosilicate, borosilicate, alumina, zirconia, tin oxide, and ytterbium fluoride.

In some embodiments, the compositions can comprise pigments or coloring agents, inhibitors, and/or initiator systems.

In preferred embodiments wherein the composition comprises a filler compound, the particle sizes of the one or more filler compounds are between about 0.001 to about 5.0 micrometers.

The present invention also relates to methods of using the compounds of formula (I) and formula (III). In preferred embodiments, the compounds are used in dental applications.

Examples of suitable dental applications include, but are not limited to dental adhesives; permanent and temporary dental resin cements; light cure and chemical cure dental nanohybrid, microhybrid, and hybrid composites; dental nanohybrid and microhybrid flowable composites; self adhesive restorative materials; temporary filling material; core build up material; and pit and fissure sealants.

In some embodiments, the compounds of the present invention, or mixtures of the compositions can be used for the fabrication of dental restorative materials, with or without filler. In some embodiments, the compounds can be place directly in the mouth and cured/polymerized in situ, or they may be fabricated outside the mouth and then adhered in place inside the mouth,

DESCRIPTION OF THE FIGURES

FIG. 9 shows a graph of conversion values of microhybrid experimental compositions using new monomers compare with conversion of microhybrid and hybrid commercial products.

FIG. 10 shows a graph of volume shrinkage values of microhybrid compositions using new monomers compare with those of microhybrid and hybrid commercial products FIG. 11 shows graphs for flexural strength and Young's modulus values of compositions using new monomers compare with those of microhybrid and hybrid commercial products Table 1 shows the values of viscosity, conversion, refractive index, volume shrinkage, flexural strength and modulus of monomers, including monomers of the present invention.

Figure 1:
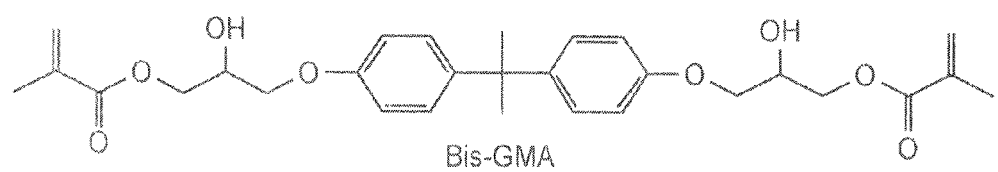
FIG. 1 shows the chemical structures of base monomers which are typically used in dental applications, such as Bis-GMA, EBPADMA and UDMA
Figure 1:
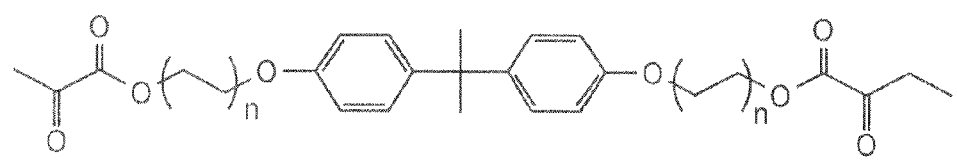
Figure 1:
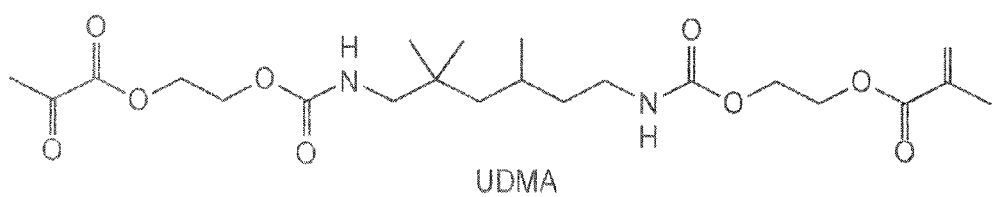
Figure 2:
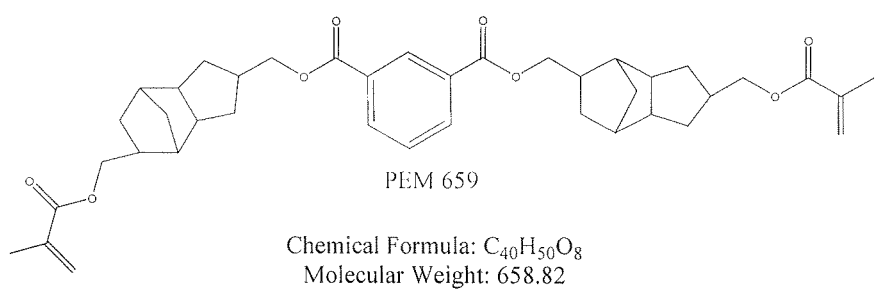
FIG. 2 shows the chemical structure of commercial available base monomers used in the present invention
Figure 2:
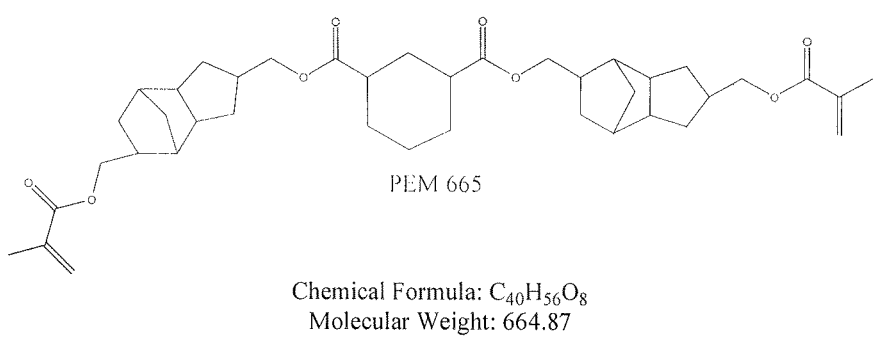

Table 2 shows the values of viscosity, conversion, refractive index, volume shrinkage, flexural strength and modulus of a variety of comonomer formulations, including those containing monomers of the present invention, as well as control resin of BisGMA/TEGDMA.

Table 3 shows the results for Mircohybrid compositions, consistency, depth of cure, conversion, volume shrinkage, flexural strength, modulus, diametral tensile strength (DTS) and compressive strength (CS).

Table 4 shows the results for Nanohybrid compositions, consistency, depth of cure, conversion, volume shrinkage, flexural strength, modulus, diametral tensile strength (DTS) and compressive strength (CS).

Table 5 shows the results for NanoDimer compositions, consistency, depth of cure, conversion, volume shrinkage, flexural strength, modulus, diametral tensile strength (DTS) and compressive strength (CS).

Table 6 shows the results for Pit and Fissure Sealant compositions, conversion, volume shrinkage, flexural strength and modulus. A commercial product is also shown for comparison.

EXAMPLES

Example 1

Materials, Methods and Instruments

FT infrared spectra of thin films between KBr crystals were recorded on a Nicolet Nexus 670 spectrometer. The $^1$H NMR and decouple $^{13}$C NMR spectra were obtained on a Varian Inova 500-MHz spectrometer using $CDCl_3$ as the solvent. Monomers viscosities were measured in pure monomers at 25° C. with a parallel-plate viscometer (CAP 2000+; Brookfield Engineering Laboratories, Stoughton, Mass.). The test was run with spindles CAP-S-01 (900 rpm) or CAP-S-06 (200 rpm) depending of resin viscosity for 15 seconds. The refractive index (nD) was measured with an Atago 1310 DR-A1 (according to Abbe's measure principle) at 20° C.

To induce photopolymerization a visible light initiator system consisting of 0.4 wt % of camphorquinone and 0.8 wt % ethyl 4-N,N-dimethylaminobenzoate were mixed with the monomers. Dynamic and static photopolymerization studies were conducted with visible light curing unit (Maxima Cure Power) in specimens prepared with a Delrin ring (inner dimensions: 1.25 mm thick and 12.5 mm diameter) sandwiched between glass cover slips irradiated for 40 s at 400 mW/cm$^2$. Dynamic and static measurements of the methacrylate monomers conversion were accomplished with transmission near-infrared (NIR) spectroscopy (Nexus 670, Nicolet). The conversion values were determined from the change in the peak area of the methacrylate overtone absorption (=C—H at 6165 cm$^{-1}$) before and after polymerization. Triplicate specimens of each monomer were polymerized and analyzed. Post-gel polymerization volumetric shrinkage was measured using an ACTA (Academic Center for Dentistry Amsterdam, Department of Materials Science, Amsterdam, The Netherlands) linometer, Shrinkage stress measurements were carried out using a device designed and fabricated at the Paffenbarger Research Center of American Dental Association Foundation (ADAF), referred as tensometer. Flexural strength and elastic modulus were determined according to ISO 4049, in a hydraulic universal testing system (Instron, Norwood, Mass.). For the measurements of compressive strength (CS) and Diametral tensile strength, 6 specimens of each material were prepared. Specimens shape and measurements were carried out according to American National Standard/American Dental Association (ANSI/ADA) Specification No. 27 for Dentistry, using the universal testing machine described above.

The composites were prepared under exclusion of light and using a speed mixer (DAC 150 FVZ) the filler was mixing in portions with the photo activated resin mixture. The amount of filler added was determined according to the desired handling properties of the material and then consistency test was performed according to ANSI/ADA Specification No. 27 described above.

FIGS. 5, 6, 7, 8, 9 and 11 and Tables 1 to 6 show the results of the experiments described above.

Example 2

No Aromatic Monomer Synthesis and Characterization

Figure 3:
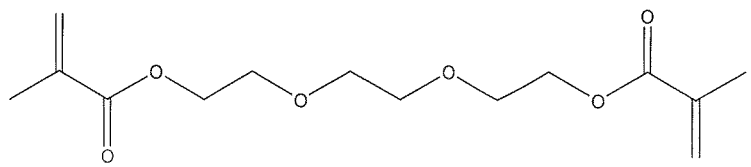
FIG. 3 shows the chemical structures of TEGDMA, HDDMA, DCP and TMPTMA, which are diluents monomers.
Figure 3:
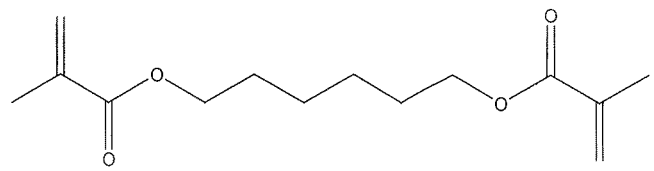
Figure 3:
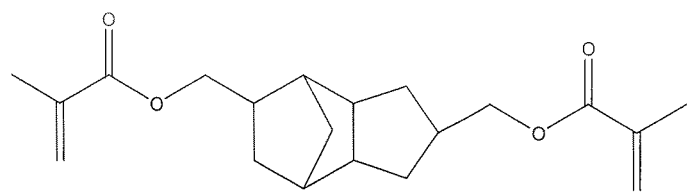
Figure 3:
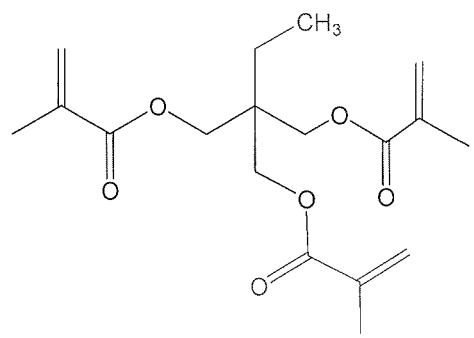
Figure 4:
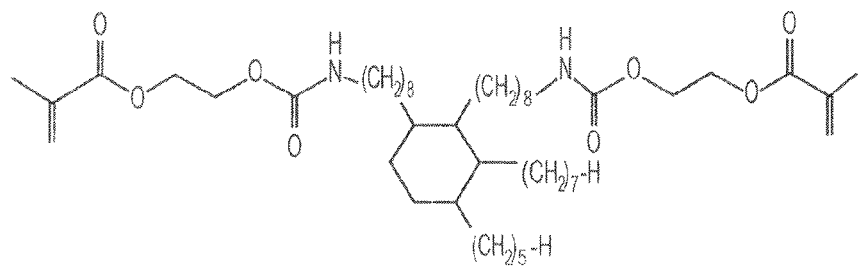
FIG. 4 shows the chemical structures of diluents monomers dimer acid type used in the present invention
Figure 4:
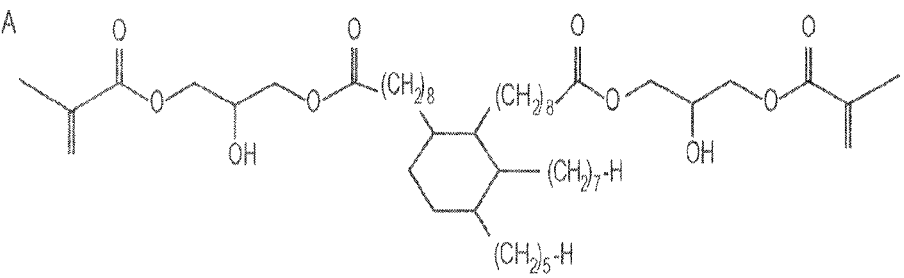
Figure 4:
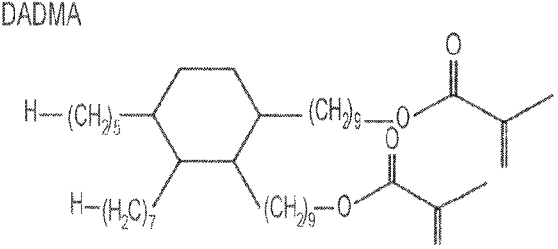
Figure 4:
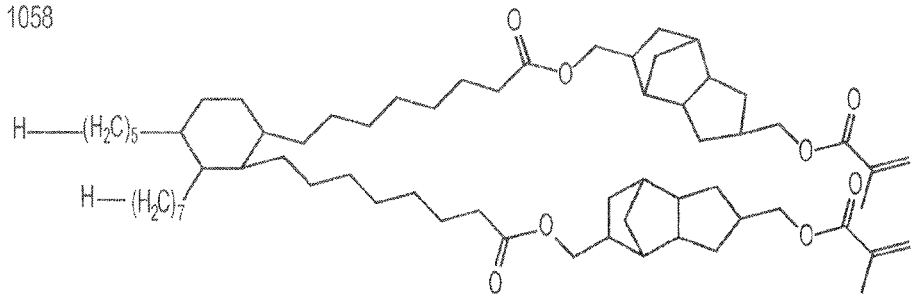
Figure 5:
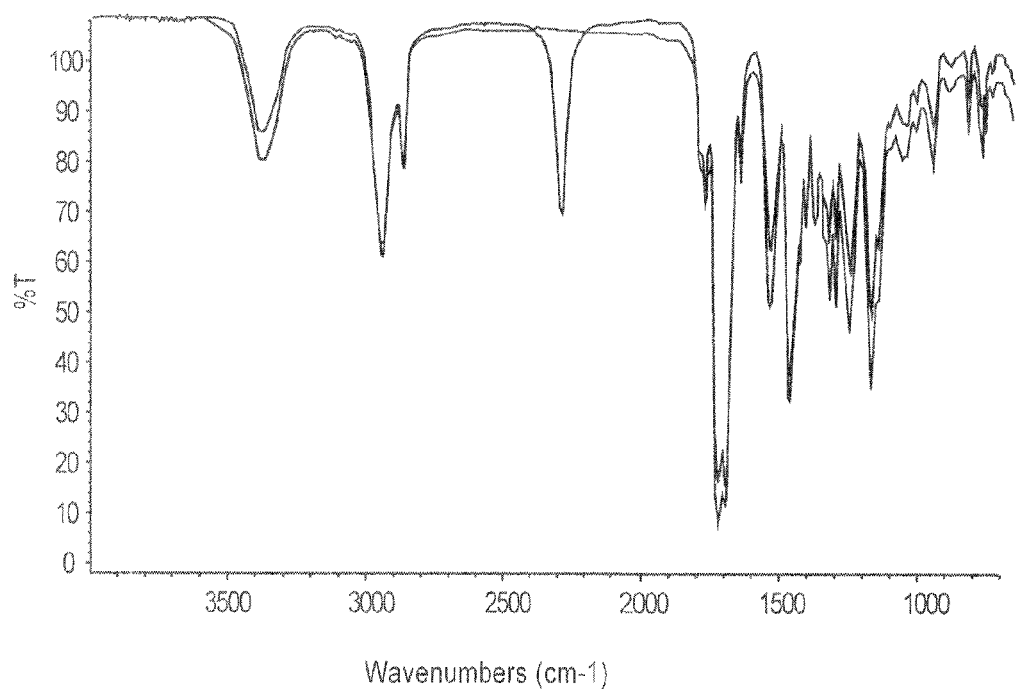
FIG. 5 is an example of the initial and final mid-IR spectra of a reaction mixture.
Figure 6:
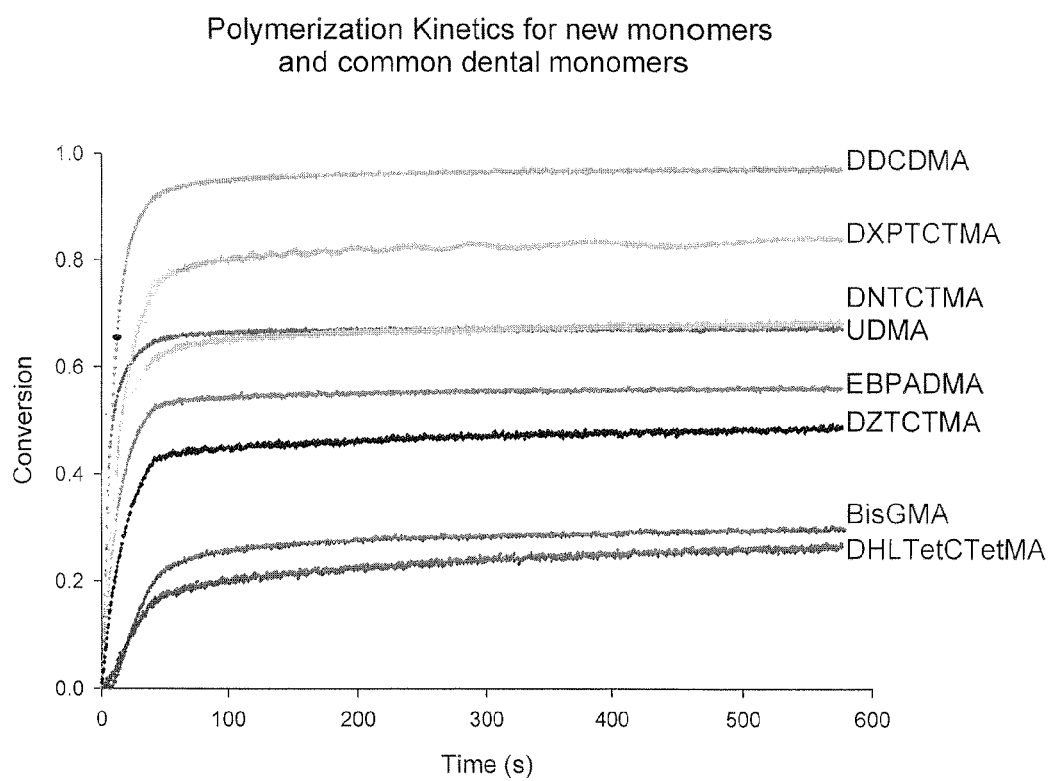
FIG. 6 shows the polymerization kinetics of monomers according to the present invention and other dimethacrylate monomers commonly used in dental restorative materials
Figure 7:
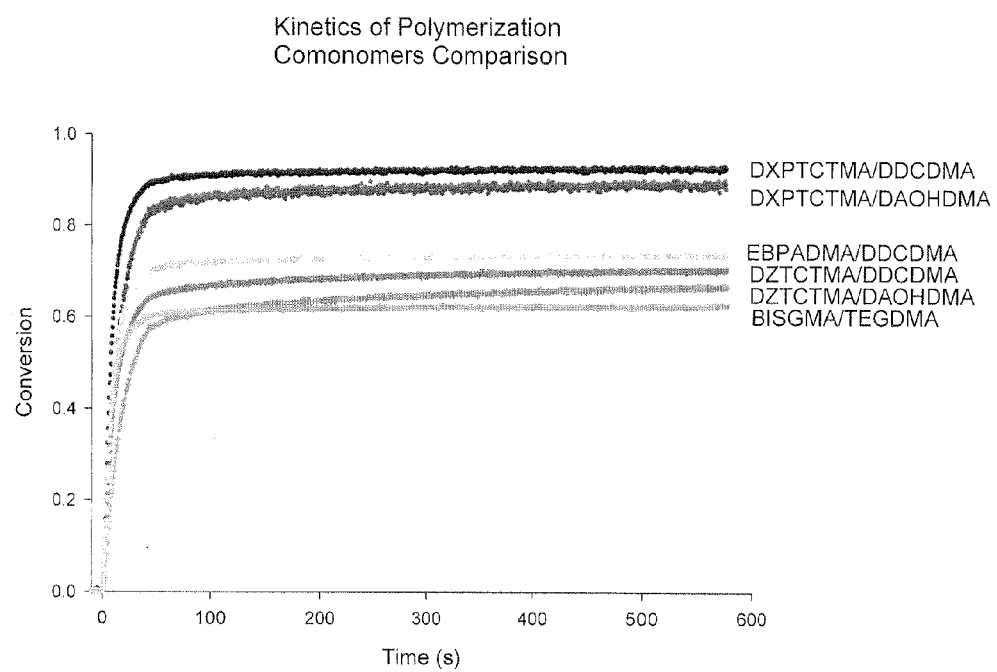
FIG. 7 shows the polymerization kinetics of copolymer systems using monomers of the present invention in dimer acid diluents, compared to a control sample of BisGMA/TEGDMA 70/30 wt %.
Figure 8:
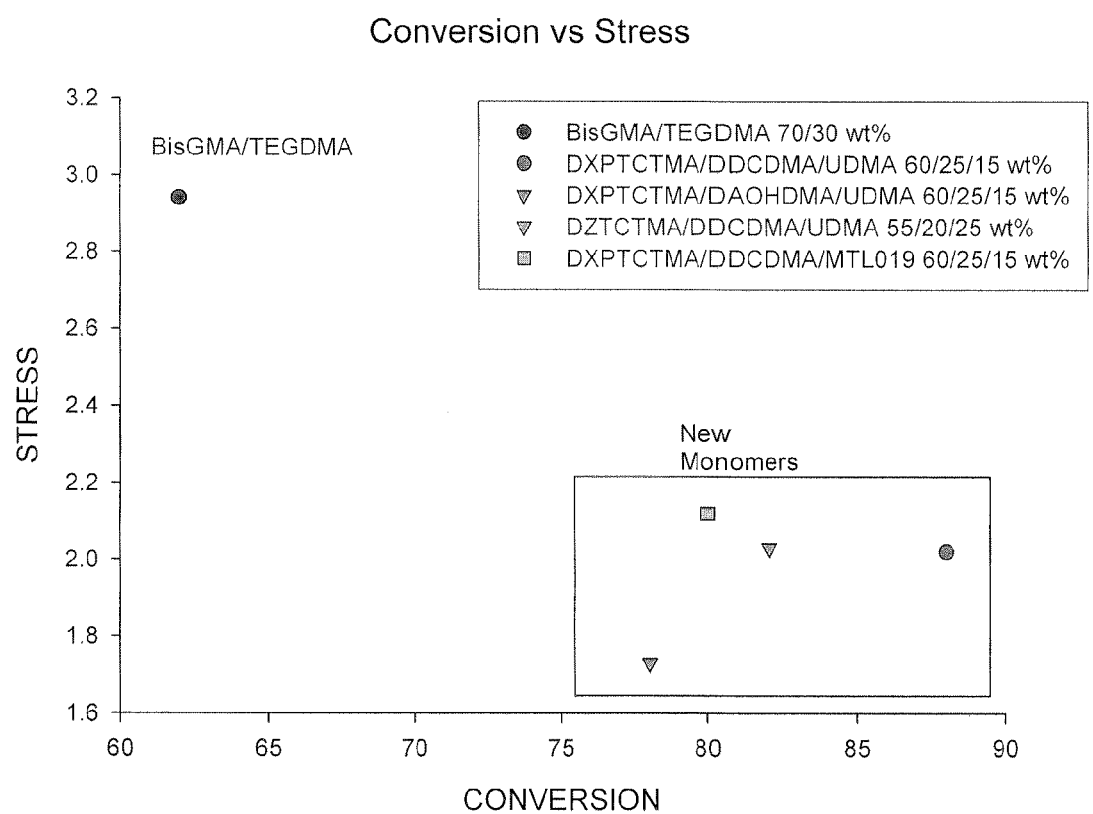
FIG. 8 shows a plot of polymerization stress versus conversion, comparing the resin formulations according to the present invention, with a control sample of BisGMA/TEGDMA 70/30 wt %.

The general procedure for the synthesis of the materials involved mixing in a three neck flask the corresponding diisocyanate, with 2.01 equivalent of hydroxyl ethyl methacrylate. 2,6-di-tert-butyl-p-cresol (BHT) was used as polymerization inhibitor. Once reagents were mixed well together an approximately 0.01 wt°/0 (base on isocyanate content) of dibutyl tindilaurate (DBTDL) were added. Reaction mixture was stirred at 50-60° C. for 18 to 24 hours. Completion of reaction was verified by FT-IR when the NCO band a 2273 cm$^{-1}$ is not observed anymore in the spectra FIG. 3. Typical reaction procedures are described below:

1. Synthesis of DNTCTMA

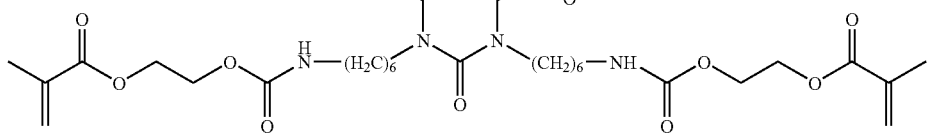

(Ia)

A mixture of Desmodur N3600 5.0458 g (0.01 mol), 4.0856 g (0.0307 mol, 3.1 equivalents) of hydroxyethyl methacrylate, 0.05 g (0.22 mmol) of 4-methoxyphenol (BHT) and a drop (10 mg) of dibutyl tin dilaurate (DBTDL) in 10 mL of methylene chloride were stirred at room temperature until isocyanate peak disappeared completely (18 h). The solvent was removed under reduced pressure to provide (Ia) as a colorless viscous oil (100% yield).

Data for 1

IR (KBr, cm$^{-1}$): v 3374 (NH), 2935-2860 (CH aliphatic), 1723-1690 (CO), 1638 (=CH$_2$)

$^1$H NMR (500 MHz, CDCl$_3$): δ 6.10, 5.56 (m, each 3H, =CH$_2$), 4.79 (s-br, 3H, NH), 4.29 (m, 12H, CH$_2$), 3.82 (m, 6H, CH$_2$), 3.13 (m, 6H, CH$_2$), 1.92 (s, 9H, CH$_3$), 1.61 (t, $^3$J(H—H)=6.4 Hz, 6H, CH$_2$), 1.48 (t, $^3$J(H—H)=6.4 Hz, 6H, CH$_2$), 1.32 (m, 12H, CH$_2$)

2. Synthesis of HDCDMA

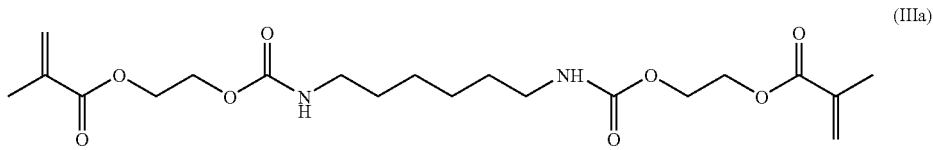 [SMILES: C=C(C)C(=O)OCCOC(=O)NCCCCCCNC(=O)OCCOC(=O)C(=C)C]
(IIIa)

A mixture of 1,6 hexamethylene diisocyanate 1.6819 g (0.01 mol), 2.6678 g (0.0205 mol, 2.1 equivalents) of hydroxyethyl methacrylate and 0.05 g (0.22 mmol) of 4-methoxyphenol (BHT) in 10 mL of methylene chloride and drop (10 mg) of dibutyl tin dilaurate (DBTDL) in 10 mL of methylene chloride were stirred at 50° C. After 18 hours Mid-IR showed completely disappearance of isocyanate peak indicating reaction completion. The reaction mixture was washed with diluted solution of hydrochloric acid (HCl, 3×20 mL), saturated solution of sodium hydroxide (NaOH) and finally with brine. Organic layer was dried using magnesium sulfate, filtered and solvent was removed first by rotaevaporation. Secondly, under reduced pressure to provide (IIIa) as a white solid.

Data for 2

IR (KBr, cm$^{-1}$): v 3325 (NH), 2945-2877 (CH aliphatic), 1715-1686 (CO), 1639 (=CH$_2$)

$^1$H NMR (500 MHz, CDCl$_3$): δ 6,15, 5.60 (m, each 2H, =CH$_2$), 4.78 (s-br, 2H, NH), 4.33 (m, 8H, CH$_2$), 3.18 (m, 4H, CH$_2$), 1.96 (s, 6H, CH$_3$), 1.50 (m, 4H, CH$_2$), 1.34 (m, 4H, CH$_2$)

3. Synthesis of DCyDCDMA

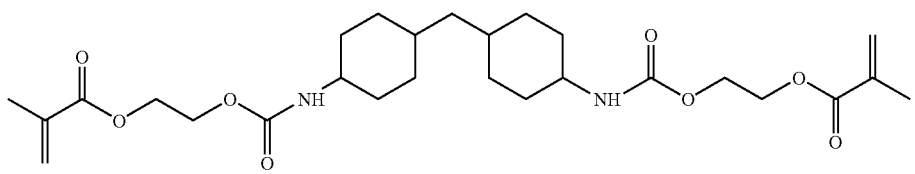
(IIIb)

Dicyclohexyl methane-4,4'-diisocyanate 2.6505 g (0.01 mol), 2.6148 g (0.0205 mol, 2.1 equivalents) of hydroxyethyl methacrylate and 0.05 g (0.22 mmol) of 4-methoxyphenol (BHT) were mixed together in 10 mL of methylene chloride. To continue, a drop (10 mg) of dibutyl tin dilaurate (DBTDL) was added and the reaction mixture was stirred at 40° C. until next day. Mid-IR showed completely disappearance of isocyanate peak. The reaction mixture was washed with diluted solution of HCl (3×20 mL), saturated solution of sodium hydroxide and finally with brine. Organic layer was dried using magnesium sulfate, filtered and solvent was removed by rotaevaporation first and then under reduced pressure to provide (IIIb) as a white waxy material.

Data for 3

IR (KBr, cm$^{-1}$): v 3358 (NH), 2928-2854 (CH aliphatic), 1721 (CO), 1637 (=CH$_2$)

$^1$H NMR (500 MHz, CDCl$_3$): δ 6.10, 5.55 (m, each 2H, =CH$_2$), 4.82 (s-br, 2H, NH), 4.27 (m, 8H, CH$_2$), 3.84 (m, 2H, CH), 1.92 (s, 6H, CH), 1.68-0.92 (m, 20H, CH$_2$)

4. Synthesis of IPDCDMA

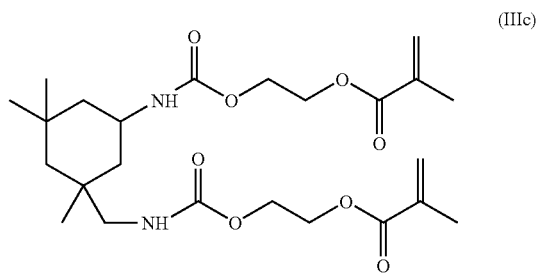 [SMILES: C=C(C)C(=O)OCCOC(=O)NCC1(C)CC(NC(=O)OCCOC(=O)C(=C)C)CC(C)(C)C1]
(IIIc)

2.2232 g (0.01 mol) of Isophorone diisocyanate (IPDI) were mixed with 2.6678 g (0.0205 mol, 2.1 equivalents) of hydroxyethyl methacrylate, 0.05 g (0.22 mmol) of 4-methoxyphenol (BHT) and a drop (10 mg) of dibutyl tin dilaurate (DBTDL) in methylene chloride (CH$_2$Cl$_2$). The reaction mixture was stirred at 40° C. until completely disappearance of isocyanate peak (24 h). The solvent was removed under reduced pressure to provide (IIIc) as a colorless viscous oil.

Data for 4

IR (KBr, cm$^{-1}$): v 3365 (NH), 2955-2850 (CH aliphatic), 1720 (CO), 1637 (=CH$_2$)

$^1$H NMR (500 MHz, CDCl$_3$): δ 6.11, 5.57 (m, each 2H, =CH$_2$), 4.82, 4.85 (s-br, each 1H, NH), 4.29 (m, 8H, CH$_2$), 3.84 (m, 1H, CH), 2.90 (m, 2H, CH$_2$), 1.93 (s, 6H, CH$_3$), 1.04 (s, 6H, 2 CH$_3$), 0.90 (s, 3H, CH$_3$)

5. Synthesis of DXPTCTMA

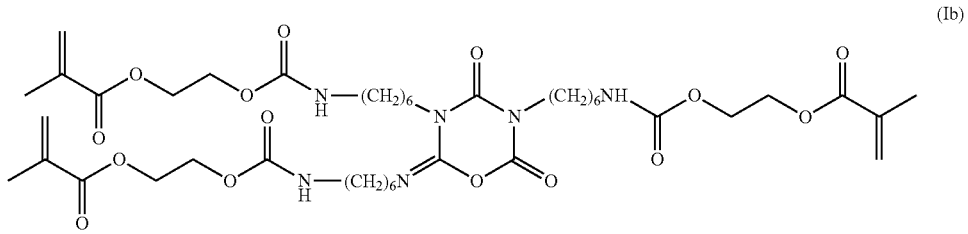
(Ib)

A mixture of Desmodur XP2410 5.0112 g (0.01 mol), 3.9977 g (0.0307 mol, 3.1 equivalents) of hydroxyethyl methacrylate, 0.05 g (0.22 mmol) of 4-methoxyphenol (BHT) and a drop (10 mg) of dibutyl tin dilaurate (DBTDL) in 10 mL of methylene chloride were stirred at room temperature until isocyanate peak disappeared completely (18 h). The solvent was removed under reduced pressure to provide (Ib) as a colorless viscous oil (yield 100%).

Data for 5

IR (KBr, $cm^{-1}$): v 3374 (NH), 2935-2860 (CH aliphatic), 1719-1693 (CO), 1638 ($=CH_2$)

$^1$H NMR (500 MHz, $CDCl_3$): δ 6.10, 5.56 (s, each 3H, $=CH_2$), 4.80 (s-br, 3H, NH), 4.28 (m, 12H, $CH_2$), 3.84 (m, 6H, $CH_2$), 3.14 (m, 8H, $CH_2$), 1.92 (s, 9H, $CH_3$), 1.60 (m, 6H, $CH_2$), 1.47 (m, 6H, $CH_2$), 1.32 (m, 12H, $CH_2$)

6. Synthesis of DZTCTMA

A mixture of Desmodur Z 6.3888 g (0.01 mol), 4.03434 g (0.031 mol, 3.1 equivalents) of hydroxyethyl methacrylate, 0.05 g (0.22 mmol) of 4-methoxyphenol (BHT) and a drop (10 mg) of dibutyl tin dilaurate (DBTDL) in 10 mL of methylene chloride were stirred at room temperature until isocyanate peak disappeared completely (48 h). The solvent was removed under reduced pressure to provide (Ic) as a colorless high viscosity material (yield 100%).

Data for 6

IR (KBr, $cm^{-1}$): v 3369 (NH), 2956 (CH aliphatic), 1719-1697 (CO), 1638 ($=CH_2$)

$^1$H NMR (500 MHz, $CDCl_3$): δ 6.12, 5.59 (m, each 3H, $=CH_2$), 4.86 (s-br, each 1H, NH), 4.29 (m, 12H, $CH_2$), 4.04 (m, 4H, $CH_2$), 3.86 (m, 3H, CH), 3.73 (m, 6H, $CH_2$), 2.90 (m, 4H, $CH_2$), 1.94 (s, 9H, $CH_3$), 1.76 (m, 6H, $CH_2$), 1.8-0.9 (several m, 37H, $CH_2$ and $CH_3$)

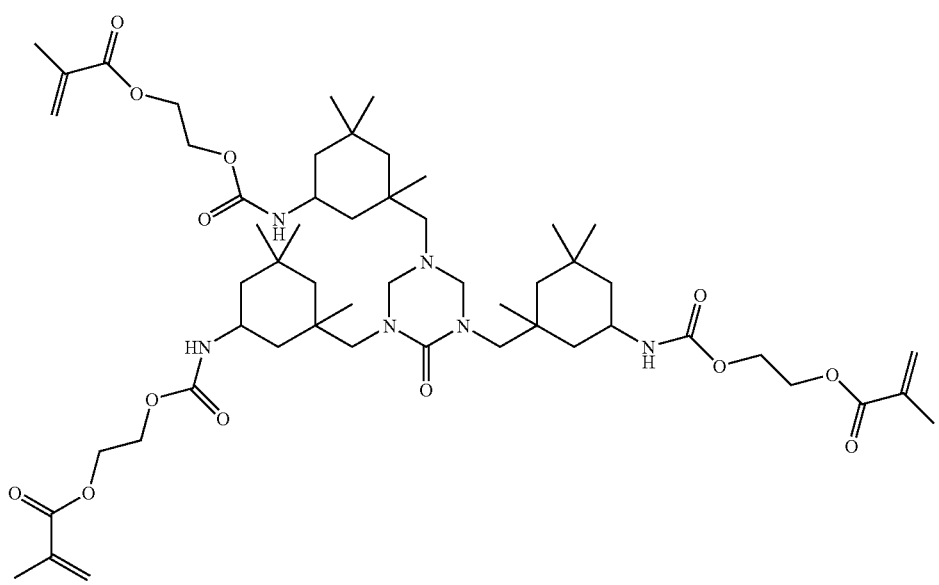
(Ic)

7. Synthesis of DHLTetCTetMA

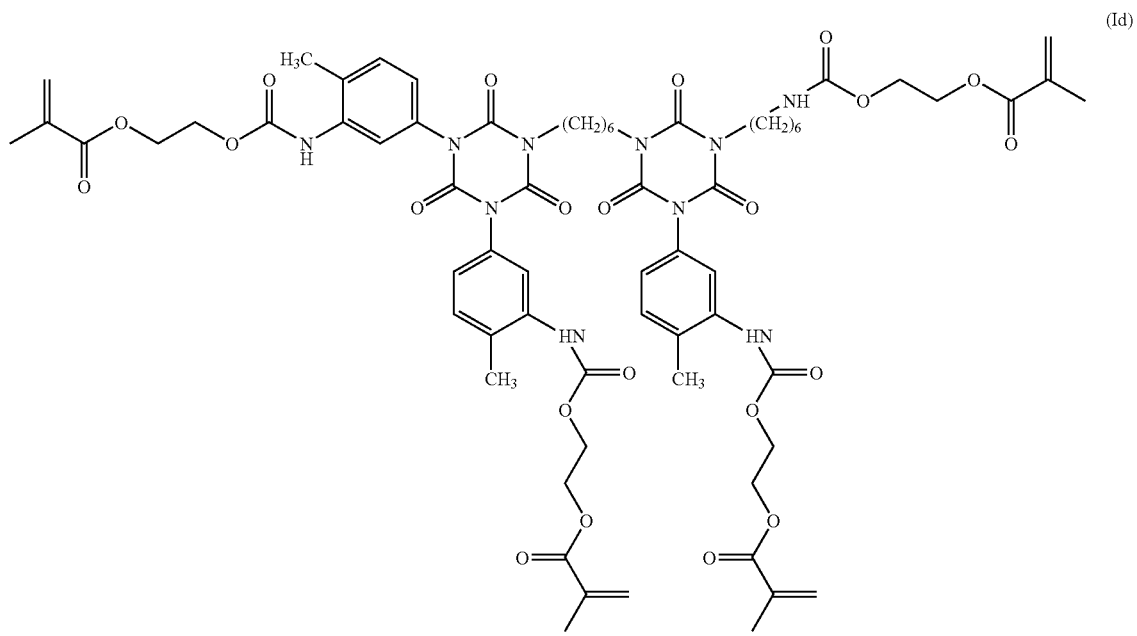

Desmodur HL 8.74 g (0.01 mol), 5.34 g (0.041 mol, 4.1 equivalents) of hydroxyethyl acrylate, 0.05 g (0.22 mmol) of 4-methoxyphenol (BHT) and a drop (10 mg) of dibutyl tin dilaurate (DBTDL) in 20 mL of methylene chloride were stirred at room temperature until isocyanate peak disappeared completely (48 h). The solvent was removed under reduced pressure to provide (Id) as a colorless highly viscous material (yield 100%).

Data for 7

IR (KBr, cm$^{-1}$): v 3360 (NH), 2956 (CH aliphatic), 1708 (CO), 1637 (=CH$_2$)

Example 3

Synthesis of Aromatic Alcohols

The synthesis of the aromatic non commercial available alcohols was carried out according to following scheme:

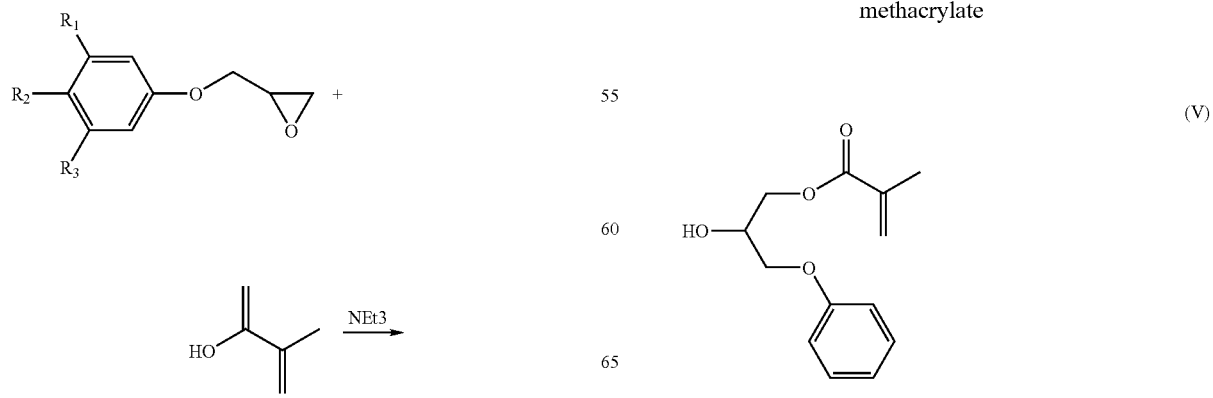

R, R2, and R3 = H, Me, tButyl, 3,5 di-tert butyl, cumyl

The general procedure involves the reaction of the aromatic oxirane and 1.05 equivalent of methacrylic acid. 2,6-di-tert-butyl-p-cresol (BHT) was used and the polymerization inhibitor. The reactions were carried out in presence of a catalytic amount of triethylamine in absence of solvent. $^1$H NMR was used to follow the reaction following disappearance of epoxide protons at 3.39, 2.93 and 2.78 ppm.

8. Synthesis of 2-hydroxy-3-phenoxypropyl methacrylate

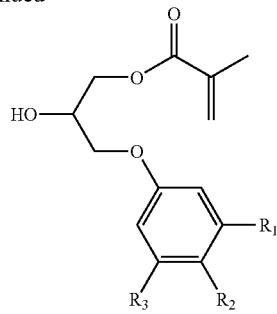

In a two neck flask equipped with a condenser under nitrogen atmosphere were placed 15.017 g (0.1 mol) of 1,2-epoxy-3-phenoxypropane, 9.039 g (0.105 mol) of methacrylic acid, 1.35 g (0.013 mol) of triethylamine and 30 mg of BHT. The reaction mixture was stirred at 60° C. ¹H NMR showed reaction completion at 24 hours. Reaction mixtures was dissolved in methylene chloride and extracted with saturated solution of sodium hydroxide (NaOH) 3×25 ml, diluted solution of acid chloride (HCl) 2×25 ml, 2×25 ml of saturated solution of sodium bicarbonate (NaHCO₃) and finally with brine 1×25 ml. Organic layer was dried over sodium sulfate (Na₂SO₄), filtered and vacuum dried. 20.14 grams (yield: 85%) of low viscosity (η=0.0891 Pa*s) amber material was obtained.

9. Synthesis of 4-tert-butylphenoxy-2-hydroxypropyl methacrylate

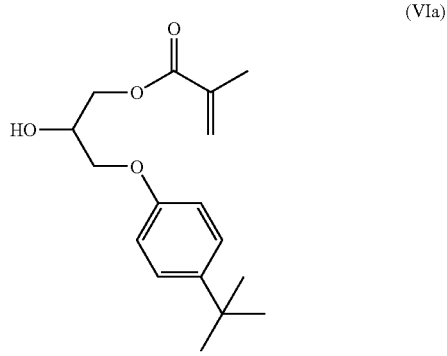 [SMILES: C=C(C)C(=O)OCC(O)COc1ccc(C(C)(C)C)cc1]

(VIa)

In a two neck flask equipped with a condenser under nitrogen atmosphere were placed 13.80 g (0.0668 mol) of 4-tert-butylphenylglycidyl ether, 6.05 g (0.070 mol) of methacrylic acid, 0.90 g (0.009 mol) of triethylamine and 30 mg of BHT. The reaction mixture was stirred at 60° C. ¹H NMR showed reaction completion at 24 hours. Reaction mixtures was dissolved in methylene chloride and extracted with saturated solution of sodium hydroxide (NaOH) 3×25 ml, diluted solution of acid chloride (HCl) 2×25 ml, 2×25 ml of saturated solution of sodium bicarbonate (NaHCO₃) and finally with brine 1×25 ml. Organic layer was dried over sodium sulfate (Na₂SO₄), filtered and vacuum dried, 14.24 grams (yield: 98%) of low viscosity (η=0.4894 Pa*s) colorless material were obtained.

10: Synthesis of 3,5-di-methylphenoxy-2-hydroxypropyl methacrylate

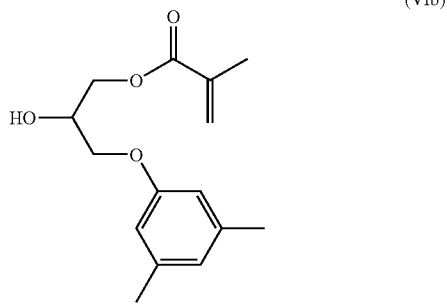

(VIb)

In a two neck flask equipped with a condenser under nitrogen atmosphere were placed 10.00 g (0.0561 mol) of 3,5-dimethylphenoxymethyl oxirane, 5.07 g (0.059 mol) of methacrylic acid, 0.90 g (0.009 mol) of triethylamine and 30 mg of BHT. The reaction mixture was stirred at 60° C. ¹H NMR showed reaction completion at 36 hours. Reaction mixtures was dissolved in methylene chloride and extracted with saturate solution of sodium hydroxide (NaOH) 3×25 ml, diluted solution of acid chloride (HCl) 2×25 ml, 2×25 ml of saturated solution of sodium bicarbonate (NaHCO₃) and finally with brine 1×25 ml. Organic layer was dried over sodium sulfate (Na₂SO₄), filtered and vacuum dried. 11.24 grams (yield: 75%) of a amber viscous oil were obtained.

11. Synthesis of 3,5-di-tert-butylphenoxy-2-hydroxypropyl methacrylate

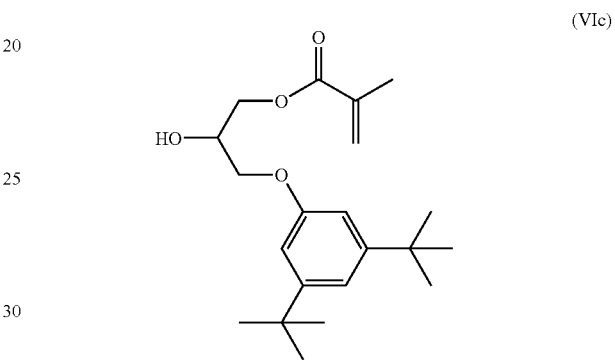

(VIc)

In a two neck flask equipped with a condenser under nitrogen atmosphere were placed 15.00 g (0.0571 mol) of 3,5-di-tert-butylphenoxymethyl oxirane, 5.16 g (0.060 mol) of methacrylic acid, 0.90 g (0.009 mol) of triethylamine and 30 mg of BHT. The reaction mixture was stirred at 60° C. ¹H NMR showed reaction completion at 24 hours. Reaction mixtures was dissolved in methylene chloride and extracted with saturated solution of sodium hydroxide (NaOH) 3×25 ml, diluted solution of acid chloride (HCl) 2×25 ml, 2×25 ml of saturated solution of sodium bicarbonate (NaHCO₃) and finally with brine 1×25 ml. Organic layer was dried over sodium sulfate (Na₂SO₄), filtered and vacuum dried. 9.36 grams (yield: 47%) of a viscous amber oil were obtained.

12. Synthesis of 2-hydroxy-3-(4-(2-phenylpropan-2-yl)phenoxy)propyl methacrylate

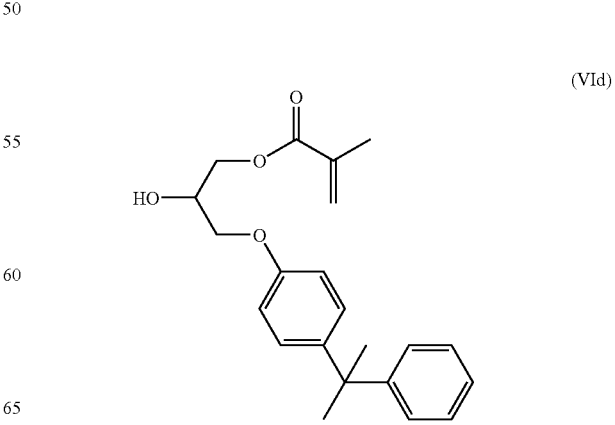

(VId)

In a two neck flask equipped with a condenser under nitrogen atmosphere were placed 12.40 g (0.0462 mol) of 4-(2-phenoxypropan-2-yl)phenoxy methyl oxirane, 4.17 g (0.049 mol) of methacrylic acid, 0.90 g (0.009 mol) of triethylamine and 30 mg of BHT. The reaction mixture was stirred at 60° C. $^1$H NMR showed reaction completion at 24 hours. Reaction mixtures was dissolved in methylene chloride and extracted with saturated solution of sodium hydroxide (NaOH) 3×25 ml, diluted solution of acid chloride (HCl) 2×25 ml, 2×25 ml of saturated solution of sodium bicarbonate (NaHCO$_3$) and finally with brine 1×25 ml. Organic layer was dried over sodium sulfate (Na$_2$SO$_4$), filtered and vacuum dried. 8.25 grams (yield: 50%) of viscous oil were obtained.

13. Synthesis of Oxirane Derives

Oxirane derives used in synthesis of compounds (VIc) and (VId) are not commercially available, so they were synthesized by reaction of the corresponding phenol with epichlorohydrin in basic reaction medium. According to procedure describe on following scheme:

Example 4

Aromatic Monomer Synthesis and Characterization

The general procedure for the synthesis of the materials involved mixing in a three neck flask the corresponding diisocyanate, with 2.05 equivalent of the aromatic alcohol for the symmetrical derives and 1.05 of each alcohol for the unsymmetrical molecules. 2,6-di-tert-butyl-p-cresol (BHT) was used as polymerization inhibitor. Once reagents were mixed well together 0.1 wt % (base on isocyanate content) of dibutyl tin dilaurate (DBTDL) were added. Reaction mixture was stirred at 50-60° C. for 18 to 24 hours. Completion of reaction was verified by FT-IR when the NCO band a 2273 cm$^{-1}$ is not observed anymore in the spectra FIG. 3. Typical reaction procedures are described below:

14. Synthesis of DTPHDMA

In a two neck flask under nitrogen atmosphere were mixed together 7.02 g (0.0417 mol) of 1,6 hexamethylene diisocyanate, 24.98 g (0.0854 mol) of (VIa) (2.05 equivalents) and 30 mg of BHT. To continue 10 mg of DBTDL were added. Reaction mixture was stirred at 50° C. until next day. Reaction product was isolate as viscous oil and can be used without further purification.

15. Synthesis of DTPDCHDMA

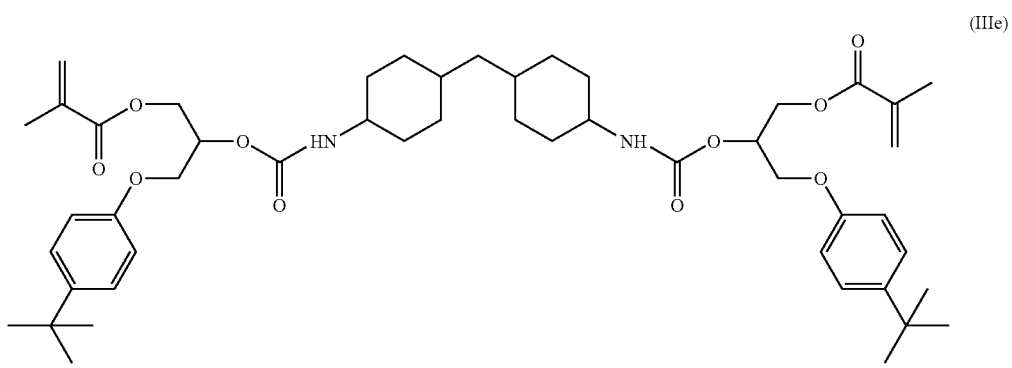 [SMILES: C=C(C)C(=O)OCC(COc1ccc(C(C)(C)C)cc1)OC(=O)NC1CCC(CC2CCC(NC(=O)OC(COC(=O)C(=C)C)COc3ccc(C(C)(C)C)cc3)CC2)CC1]

In a two neck flask under nitrogen atmosphere were mixed together 10.93 (0.0417 mol) of dicyclohexylmethane-4,4'-diisocyanate, 25.00 g (0.0855 mol) of (VIa) (2.05 equivalents) and 30 mg of BHT. To continue 10 mg of DBTDL were added. Reaction was stirred at 50° C. until next day. Reaction product was isolate as viscous oil and can be used without further purification.

16. Synthesis of DPHDMA

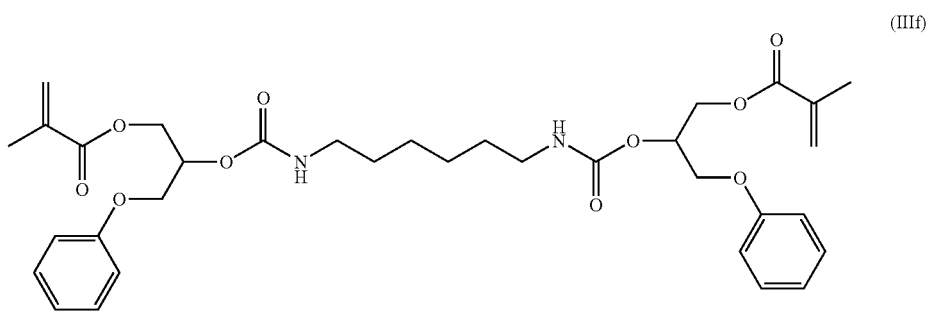 [SMILES: C=C(C)C(=O)OCC(COc1ccccc1)OC(=O)NCCCCCCNC(=O)OC(COC(=O)C(=C)C)COc1ccccc1]

In a two neck flask under nitrogen atmosphere were mixed together 4.00 g (0.0238 mol) of 1,6 hexamethylene diisocyanate, 11.80 g (0.0499 mol) of (V) (2.05 equivalents) and 30 mg of BHT. To continue 10 mg of DBTDL were added. Reaction mixture was stirred at 50° C. until next day. Reaction product was isolate as viscous oil and can be used without further purification.

17. Synthesis of TBPPHDMA

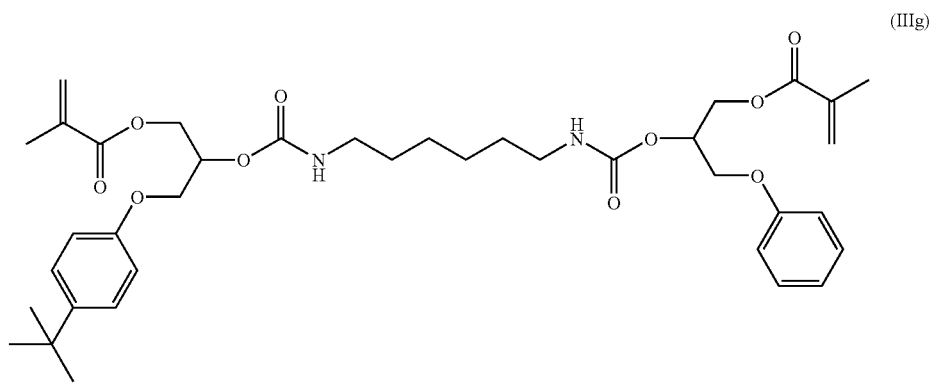 [SMILES: C=C(C)C(=O)OCC(COc1ccccc1)OC(=O)NCCCCCCNC(=O)OC(COC(=O)C(=C)C)COc1ccc(C(C)(C)C)cc1]

In a two neck flask under nitrogen atmosphere were mixed together 28.00 g (0.1665 mol) of 1,6 hexamethylene diisocyanate, 41.30 g (0.1748 mol) of (V) (1.05 equivalents), 51.11 g (0.1748 mol) of (VIa) and 30 mg of BHT. To continue 10 mg of DBTDL were added. Reaction mixture was stirred at 50° C. until next day. Reaction product was isolated as viscous oil and can be used without further purification.

18. Synthesis of TBPPDCHDMA

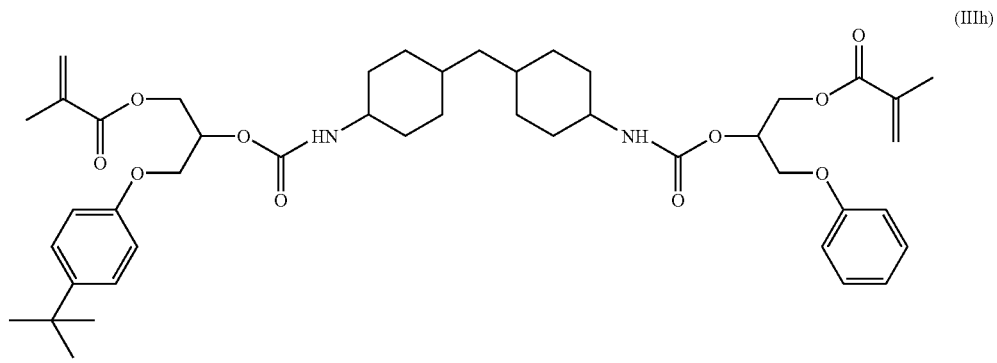 [SMILES: C=C(C)C(=O)OCC(COc1ccccc1)OC(=O)NC1CCC(CC2CCC(NC(=O)OC(COC(=O)C(=C)C)COc3ccc(C(C)(C)C)cc3)CC2)CC1]
(IIIh)

In a two neck flask under nitrogen atmosphere were mixed together 43.68 (0.1665 mol) of dicyclohexylmethane-4,4'-diisocyanate, 41.30 g (0.1748 mol) of (V) (1.05 equivalents), 51.11 g (0.1748 mol) of (VIa) and 30 mg of BHT. To continue 10 mg of DBTDL were added. Reaction mixture was stirred at 50° C. until next day. Reaction product was isolated as viscous oil and can be used without further purification.

19. Synthesis of TTPHDMA

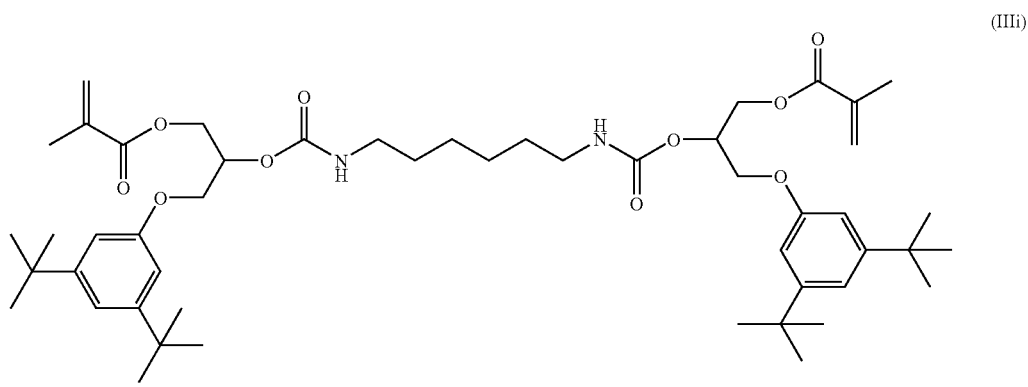 [SMILES: C=C(C)C(=O)OCC(COc1cc(C(C)(C)C)cc(C(C)(C)C)c1)OC(=O)NCCCCCCNC(=O)OC(COC(=O)C(=C)C)COc1cc(C(C)(C)C)cc(C(C)(C)C)c1]
(IIIi)

In a two neck flask under nitrogen atmosphere were mixed together 16.00 g (0.095 mol) of 1,6 hexamethylene diisocyanate, 67.95 g (0.1950 mol) of (VIc) (2.05 equivalents), and 30 mg of BHT. To continue 10 mg of DBTDL were added. Reaction mixture was stirred at 50° C. until next day. Reaction product was isolated as viscous oil and can be used without further purification.

20. Synthesis of TTPDCHDMA

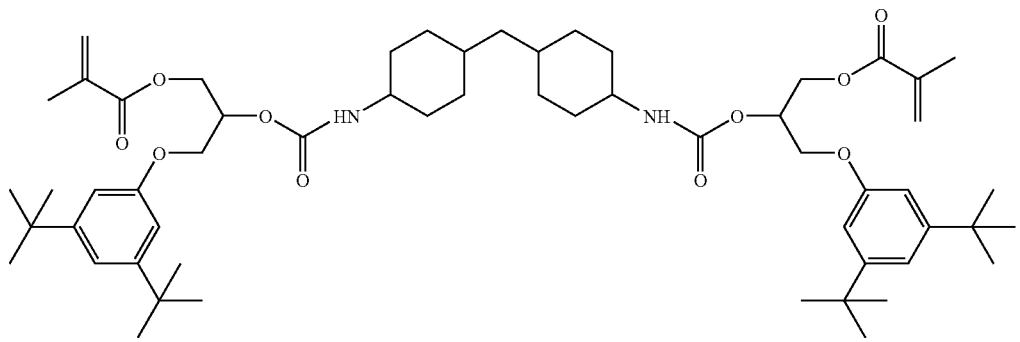

(IIIj)

In a two neck flask under nitrogen atmosphere were mixed together 9.98 g (0.038 mol) of dicyclohexylmethane-4,4'-diisocyanate, 27.18 g (0.078 mol) of (VIc) (2.05 equivalents), and 30 mg of BHT. To continue 10 mg of DBTDL were added. Reaction mixture was stirred at 50° C. until next day. Reaction product was isolated as viscous oil and can be used without further purification

21. Synthesis of HDCHDMA

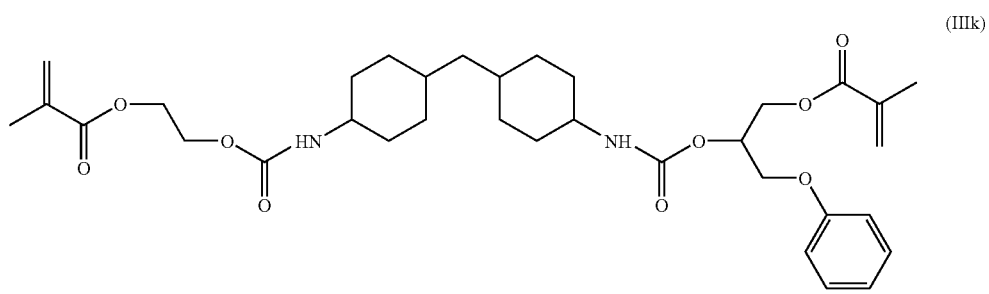 [SMILES: C=C(C)C(=O)OCCOC(=O)NC1CCC(CC2CCC(NC(=O)OC(COC(=O)C(=C)C)COc3ccccc3)CC2)CC1]

(IIIk)

In a two neck flask under nitrogen atmosphere were mixed together 13.00 g (0.050 mmol) of dicyclohexylmethane-4,4'-diisocyanate, 6.58 g (0.051 mol) of hydroxyethyl methacrylate (1.02 equivalents), 11.93 g (0.051 mol) of (V) (1.02 equivalents), and 30 mg of BHT. To continue 10 mg of DBTDL were added. Reaction mixture was stirred at 50° C. until next day. Reaction product was isolated as viscous oil and can be used without further purification

22. Synthesis of PDCHDMA

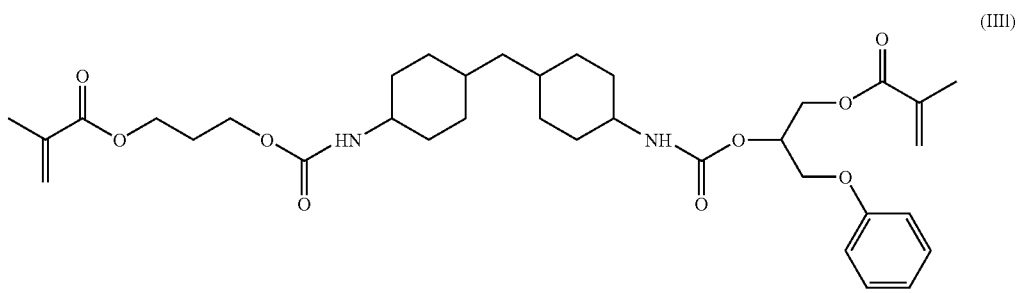 [SMILES: C=C(C)C(=O)OCCCOC(=O)NC1CCC(CC2CCC(NC(=O)OC(COC(=O)C(=C)C)COc3ccccc3)CC2)CC1]

(IIIl)

In a two neck flask under nitrogen atmosphere were mixed together 13.00 g (0.050 mol) of dicyclohexylmethane-4,4'-diisocyanate, 7.28 g (0.051 mol) of hydroxypropyl methacrylate (1.02 equivalents), 11.93 g (0.051 mol) of (V) (1.02 equivalents), and 30 mg of BHT. To continue 10 mg of DBTDL were added. Reaction mixture was stirred at 50° C. until next day. Reaction product was isolated as viscous oil and can be used without further purification 23. Synthesis of TMTBPNHDMA

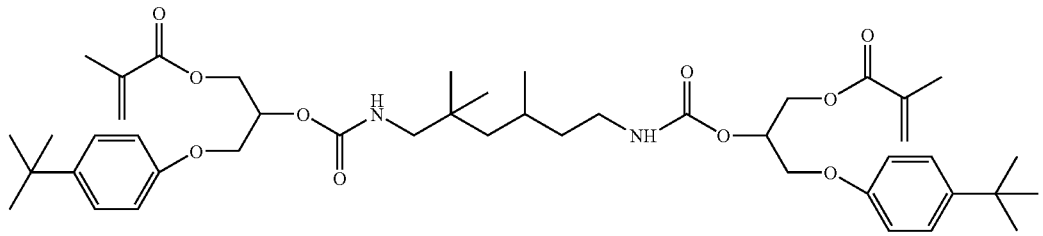

(IIIm)

In a two neck flask under nitrogen atmosphere were mixed together 21.00 g (0.0998 mol) of trimethyl-1,6-diisocyanate isomer mixture, 59.81 g (0.2046 mol) of (VIa) (2.05 equivalents) and 30 mg of BHT. To continue 10 mg of DBTDL were added. Reaction mixture was stirred at 50° C. until next day. Reaction product was isolated as viscous oil and can be used without further purification 24. Synthesis of TMPNHDMA

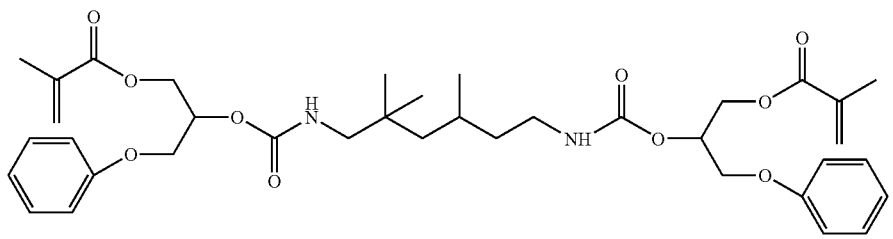

(IIIn)

In a two neck flask under nitrogen atmosphere were mixed together 21.00 g (0.0998 mol) of trimethyl-1,6-diisocyanate isomer mixture, 48.34 g (0.2046 mol) of (Va) (2.05 equivalents) and 30 mg of BHT. To continue 10 mg of DBTDL were added. Reaction mixture was stirred at 50° C. until next day. Reaction product was isolated as viscous oil and can be used without further purification.

25. Synthesis of TMTBPPNHDMA

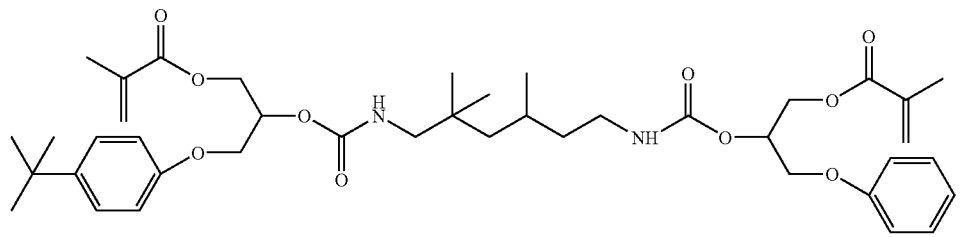

(IIIo)

In a two neck flask under nitrogen atmosphere were mixed together 21.00 g (0.0998 mol) of trimethyl-1,6-diisocyanate isomer mixture, 24.05 g (0.1018 mol) of (V) (1.02 equivalents), 29.76 g (1.02 equivalents) of (VIa) and 30 mg of BHT, To continue 10 mg of DBTDL were added. Reaction mixture was stirred at 50° C. until next day. Reaction product was isolated as viscous oil and can be used without further purification.

Example 3

In a vial with exclusion of light the initiator system and the components were dissolved, at temperatures not above 50° C.

The following chart shows examples of resin compositions, with the amounts of the components in wt %.

| Components | Composition 1 | Composition 2 | Composition 3 | Composition 4 | Composition 5 |
|---|---|---|---|---|---|
| Uninul 3000 | 0.75 | 0.75 | 0.75 | 0.75 | 0.75 |
| DXPTCTMA | 58.68 | 53.79 | 53.79 | 58.68 | 48.90 |
| DDCDMA | 24.45 | 24.45 | 19.56 | 19.56 | 24.45 |
| UDMA | 14.67 | 19.56 | 24.45 | 19.56 | 19.56 |
| BHT[b] | 0.18 | 0.18 | 0.18 | 0.18 | 0.18 |
| Ethyl-4 Dimethyl amino benzoate | 0.85 | 0.85 | 0.85 | 0.85 | 0.85 |
| Camphorquinone | 0.41 | 0.41 | 0.41 | 0.41 | 0.41 |

[b]2,6-Di-tert-butyl-p-cresol

Example 4

In a vial with exclusion of light the initiator system and the components were dissolved at temperatures not above 50° C.

The following chart shows examples of resin compositions, with the amounts of the components in wt %.

| Components | Composition 6 | Composition 7 | Composition 8 | Composition 9 | Composition 10 |
|---|---|---|---|---|---|
| Uninul 3000 | 0.75 | 0.75 | 0.75 | 0.75 | 0.75 |
| DZTCTMA | 58.68 | 53.79 | 53.79 | 58.68 | 48.90 |
| DDCDMA | 24.45 | 24.45 | 19.56 | 19.56 | 24.45 |
| UDMA | 14.67 | 19.56 | 24.45 | 19.56 | 19.56 |
| BHT[b] | 0.18 | 0.18 | 0.18 | 0.18 | 0.18 |
| Ethyl-4 Dimethyl amino benzoate | 0.85 | 0.85 | 0.85 | 0.85 | 0.85 |
| Camphorquinone | 0.41 | 0.41 | 0.41 | 0.41 | 0.41 |

[b]2,6-Di-tert-butyl-p-cresol

Example 5

In a vial with exclusion of light the initiator system and the components were dissolved at temperatures not above 50° C.

The following chart shows examples of resin compositions, with the amounts of the components in wt %.

| Components | Composition 11 | Composition 12 | Composition 13 | Composition 14 | Composition 15 |
|---|---|---|---|---|---|
| Uninul 3000 | 0.75 | 0.75 | 0.75 | 0.75 | 0.75 |
| DZTCTMA | 58.68 | 53.79 | 53.79 | 58.68 | 48.90 |
| HDDMA[a] | 24.45 | 24.45 | 19.56 | 19.56 | 24.45 |
| UDMA | 14.67 | 19.56 | 24.45 | 19.56 | 19.56 |
| BHT[b] | 0.18 | 0.18 | 0.18 | 0.18 | 0.18 |
| Ethyl-4 Dimethyl amino benzoate | 0.85 | 0.85 | 0.85 | 0.85 | 0.85 |
| Camphorquinone | 0.41 | 0.41 | 0.41 | 0.41 | 0.41 |

[a]1,6 hexanedioldimethacrylate
[b]2,6-Di-tert-butyl-p-cresol

Example 6

The following chart shows examples of microhybrid composite, with the amounts of the components in wt %.

| | Microhybrid Composite | | |
|---|---|---|---|
| Components | Composition 16 | Composition 17 | Composition 18 |
| Uninul 3000 | 0.19 | 0.19 | 0.19 |
| TBPPHDMA | 21.2 | 20.53 | 19.87 |
| HDDMA[a] | 5.30 | 5.96 | 6.63 |
| BHT[b] | 0.18 | 0.18 | 0.18 |
| Ethyl-4 Dimethyl amino benzoate | 0.047 | 0.85 | 0.85 |

-continued

Microhybrid Composite

| Components | Composition 16 | Composition 17 | Composition 18 |
|---|---|---|---|
| Camphorquinone | 0.11 | 0.41 | 0.41 |
| Barium Glasses | 68.86 | 68.86 | 68.86 |
| Silica | 4.08 | 4.08 | 4.08 |
| Pigments Brown, Yellow and TiO2 | <0.1 | <0.1 | <0.1 |

[a] 1,6 hexanedioldimethacrylate
[b] 2,6-Di-tert-butyl-p-cresol

Example 7

The following charts show examples of nanohybrid radio opaque composite, with the amounts of the components in wt %.

Nanohybrid Radio Opaque Composite

| Components | Composition 19 | Composition 20 | Composition 21 | Composition 22 |
|---|---|---|---|---|
| Uninul 3000 | 0.19 | 0.19 | 0.19 | 0.19 |
| TBPPHDMA | 15.5 | 14.50 | 13.54 | 15.5 |
| HDDMA[a] | 3.87 | 4.84 | 5.80 | 3.87 |
| BHT[b] | 0.18 | 0.18 | 0.18 | 0.18 |
| Ethyl-4 Dimethyl amino benzoate | 0.047 | 0.85 | 0.85 | 0.047 |
| Camphorquinone | 0.11 | 0.41 | 0.41 | 0.11 |
| Barium glass | 68.56 | 68.86 | 68.86 | 68.56 |
| Ytterbium glass | 8.06 | | | 8.06 |
| Silica | 4.03 | 4.03 | 4.03 | 4.03 |
| Pigments Brown, Yellow and TiO2 | <0.1 | <0.1 | <0.1 | <0.1 |

[a] 1,6 hexanedioldimethacrylate
[b] 2,6-Di-tert-butyl-p-cresol

| Components | Composition 23 | Composition 24 | Composition 25 | Composition 26 |
|---|---|---|---|---|
| Uninul 3000 | 0.19 | 0.19 | 0.19 | 0.19 |
| TBPPHDMA | 18.6 | 17.37 | 18.6 | 17.37 |
| HDDMA[a] | 4.68 | 5.87 | 4.68 | 5.87 |
| BHT[b] | 0.18 | 0.18 | 0.18 | 0.18 |
| Ethyl-4 Dimethyl amino benzoate | 0.047 | 0.85 | 0.047 | 0.85 |
| Camphorquinone | 0.11 | 0.41 | 0.11 | 0.41 |
| Barium glass | 60.80 | 60.80 | 60.80 | 60.80 |
| Ytterbium glass | 11.40 | 11.40 | 11.40 | 11.40 |
| Silica | 3.80 | 3.80 | 3.80 | 3.80 |
| Pigments Brown, Yellow and TiO2 | <0.1 | <0.1 | <0.1 | <0.1 |

[a] 1,6 hexanedioldimethacrylate
[b] 2,6-Di-tert-butyl-p-cresol

| Components | Composition 27 | Composition 28 | Composition 29 | Composition 30 |
|---|---|---|---|---|
| Uninul 3000 | 0.19 | 0.19 | 0.19 | 0.19 |
| TBPPHDMA | 16.18 | 17.37 | 16.18 | 17.37 |
| DDCDMA | 7.06 | 5.87 | 7.06 | 5.87 |
| BHT[a] | 0.18 | 0.18 | 0.18 | 0.18 |
| Ethyl-4 Dimethyl amino benzoate | 0.85 | 0.85 | 0.85 | 0.85 |

-continued

| Components | Composition 27 | Composition 28 | Composition 29 | Composition 30 |
|---|---|---|---|---|
| Camphorquinone | 0.41 | 0.41 | 0.41 | 0.41 |
| Ytterbium Glasses | 60.80 | 60.80 | 60.80 | 60.80 |
| Silica | 11.40 | 11.40 | 11.40 | 11.40 |
| Pigments Brown, Yellow and TiO2 | 3.80 | 3.80 | 3.80 | 3.80 |

[a] 2,6-Di-tert-butyl-p-cresol

Example 8

Pit and Fissure Sealant

The following chart show examples of pit and fissure sealants formulations, amounts of components are in wt %.

| Components | Composition 31 | Composition 32 | Composition 33 |
|---|---|---|---|
| Uninul 3000 | 0.51 | 0.51 | 0.51 |
| TBPPHDMA | 63.43 | 63.43 | 63.43 |
| DDCDMA | 18.85 | 16.28 | 12.00 |
| HDDMA[a] | 1.71 | 4.28 | 8.57 |
| Isobornyl methacrylate | 14.28 | 14.28 | 14.28 |
| BHT[b] | 0.17 | 0.17 | 0.17 |
| Ethyl-4 Dimethyl amino benzoate | 0.68 | 0.68 | 0.68 |
| Camphorquinone | 0.34 | 0.34 | 0.34 |

[a] 1,6 hexanedioldimethacrylate
[b] 2,6-Di-tert-butyl-p-cresol

| Components | Composition 34 | Composition 35 | Composition 36 |
|---|---|---|---|
| Uninul 3000 | 0.51 | 0.51 | 0.51 |
| TBPPHDMA | 63.43 | 63.43 | 63.43 |
| DDCDMA | 18.85 | 16.28 | 12.00 |
| TMPTMA[a] | 1.71 | 4.28 | 8.57 |
| Isobornyl methacrylate | 14.28 | 14.28 | 14.28 |
| BHT[b] | 0.17 | 0.17 | 0.17 |
| Ethyl-4 Dimethyl amino benzoate | 0.68 | 0.68 | 0.68 |
| Camphorquinone | 0.36 | 0.36 | 0.36 |

[a] Trimethylolpropane trimethacrylate
[b] 2,6-Di-tert-butyl-p-cresol

| | Composition 37 | Composition 38 | Composition 39 |
|---|---|---|---|
| Uninul 3000 | 0.51 | 0.51 | 0.51 |
| TBPPHDMA | 63.43 | 63.43 | 63.43 |
| DDCDMA | 18.85 | 16.28 | 12.00 |
| DCP[a] | 1.71 | 4.28 | 8.57 |
| Isobornyl methacrylate | 14.28 | 14.28 | 14.28 |
| BHT[b] | 0.17 | 0.17 | 0.17 |
| Ethyl-4 Dimethyl amino benzoate | 0.68 | 0.68 | 0.68 |
| Camphorquinone | 0.36 | 0.36 | 0.36 |

[a] Tricyclodecane dimethanol dimethacrylate
[b] 2,6-Di-tert-butyl-p-cresol

TABLE 1

| MATERIAL NAME | Viscosity Pa*s | Conversion (%) | nD | Volume Shrinkage (%) | FS (MPa) | Modulus (MPa) |
|---|---|---|---|---|---|---|
| DXPTCTMA | 8.74(50° C.) | 81 ± 2 | 1.4776 | 5.53 ± 0.10 | 31 ± 3 | 669 ± 72 |
| DNTCTMA | 7.20(50° C.) | 68 | 1.489 | 4.40 ± 0.10 | 86 ± 4 | 1715 ± 74 |
| DZTCTMA | 5.36(50° C.) | 56 ± 3 | 1.4750 | 3.50 ± 0.40 | | |
| DHLTetCTetMA | | 32 | | | | |
| DTPHDMA | 4.05(50° C.) | 76 ± 3 | 1.513 | 3.03 ± 0.30 | 56 ± 5 | 1641 ± 45 |
| DPHDMA | 15.26(50° C.) | 78 ± 1 | 1.5210 | 4.20 ± 0.10 | 83 ± 12 | 1931 ± 239 |
| TBPPDCHDMA | 2.54(50° C.) | 63 ± 1 | 1.5278 | 3.20 ± 0.20 | 42 ± 8 | 1272 ± 144 |
| TBPPHDMA | 11.92(50° C.) | 76 ± 2 | 1.5163 | 3.80 ± 0.20 | 91 ± 9 | 2162 ± 203 |
| DXProTMA | 7.27(50° C.) | 63 ± 1 | 1.4950 | 3.50 ± 0.10 | 96 ± 7 | 1901 ± 130 |
| HDCHDMA | | 49 ± 1 | 1.5195 | 1.80 ± 0.20 | | |
| PDCHDMA | | 29 ± 1 | 1.5178 | 1.90 ± 0.30 | | |
| DDCDMA | 1.91 | 94 ± 1 | 1.4840 | 4.32 ± 0.06 | 13 ± 1 | 158 ± 29 |
| DAOHDMA | 0.53 | 84 | 1.4861 | | | |
| Bis-GMA | 14.62(50° C.) | 30 | 1.5456 | 3.43 | 86 ± 13lit | |
| EBPADMA | 0.90 | 56 ± 2 | 1.5421 | 5.16 ± 0.06 | 86 ± 1 | 1766 ± 96 |
| UDMA | 8.48 | 67 ± 1 | 1.4841 | 6.14 ± 0.05 | 90 ± 11 | 2246 ± 208 |
| TEGDMA | 0.0169 | 63 ± 1 | 1.4603 | 4.91 ± 0.05 | 31 ± 9 | 737 ± 61 |
| HDDMA (Hexanediol dimethacrylate) | 0.007 | 60 ± 1 | 1.4578 | 5.37 ± 0.08 | | | nD = Refractive index at 20° C.

TABLE 2

| Formulations | Viscosity Pa*s | Conversion (%) | nD | Volume Shrinkage (%) | FS (MPa) | Modulus (MPa) |
|---|---|---|---|---|---|---|
| Bis-GMA/TEGDMA 70/30 wt % (CONTROL) | 1.73 | 62 | | 6.33 | 97 ± 7 | 2155 ± 104 |
| EBPADMA/DDCDMA 70/30 wt % | | 74 | | 5.27 | 74 ± 5 | 1479 ± 101 |
| DXPTCTMA/DDCDMA 70/30 wt % | 1.88 | 90 | | 5.31 | 30 ± 2 | 576 ± 44 |
| DXPTCTMA/DAOHDMA 70/30 wt % | 2.1 | 86 | | 3.73 | 13 ± 3 | 180 ± 28 |
| TBPPHDMA/HDDMA 95/5 wt % | 9.15 ± 0.00 | 75.3 ± 0.4 | | 4.7 ± 0.2 | 43 ± 3 | 1003 ± 70 |
| TBPPHDMA/HDDMA 85/15 wt % | 2.35 ± 0.01 | 76.9 ± 0.4 | | 5.0 ± 0.1 | 45 ± 2 | 919 ± 86 |
| TBPPHDMA/HDDMA 80/20 wt % | 1.68 ± 0.02 | 83.8 ± 0.6 | | 6.0 ± 0.1 | 90 ± 7 | 2090 ± 170 |
| DTPHDMA/HDDMA 85/15 wt % | 10.46 ± 0.04 | 73.7 ± 0.2 | | 4.2 ± 0.1 | 47 ± 5 | 937 ± 280 |
| DTPHDMA/HDDMA 80/20 wt % | 4.92 ± 0.02 | 74.9 ± 0.4 | | 5.0 ± 0.2 | 55 ± 7 | 1231 ± 205 |
| DTPHDMA/HDDMA 75/25 wt % | 2.16 ± 0.02 | 73.5 ± 0.8 | | 5.30 ± 0.2 | 53 ± 2 | 1160 ± 59 |
| DTPHDMA/DCP 80/20 wt % | 5.60 ± 0.02(50° C.) | 54 ± 2 | | 2.65 ± 0.10 | 53 ± 11 | 1514 ± 160 |
| DTPHDMA/DCP 75/25 wt % | 2.94 ± 0.05(50° C.) | 61.0 ± 1 | | 3.04 ± 0.12 | 40 ± 2 | 1524 ± 339 |
| DTPHDMA/DCP 70/30 wt % | 2.00 ± 0.02(50° C.) | 55.5 ± 0.3 | | 3.11 ± 0.20 | 69 ± 5 | 1827 ± 231 |
| TBPPHDMA/DCP 80/20 wt % | 1.81 ± 0.02(50° C.) | 63 ± 0 | | 3.36 ± 0.18 | 79 ± 4 | 1729 ± 192 |
| TBPPHDMA/DCP 75/25 wt % | 1.50 ± 0.07(50° C.) | 62 ± 1 | | 4.63 ± 0.32 | 67 ± 4 | 1604 ± 35 |
| TBPPHDMA/HDDMA 78/22 wt % | 8.2 ± 0.2(50° C.) | 51 ± 2 | | 3.04 ± 0.15 | 76 ± 6 | 1756 ± 210 |
| HDCHDMA/HDDMA 70/30 wt % | 2.54 ± 0.02 | 66 ± 0.63 | | 5.54 ± 0.39 | | |
| HDCHDMA/HDDMA 75/25 wt % | 6.53 ± 0.04 | 62 ± 0.31 | | 4.85 ± 0.51 | 55 ± 3 | 984 ± 17 |
| PDCHDMA/HDDMA 70/30 wt % | 3.2 ± 0.06 | 64 ± 0.87 | | 7.08 ± 0.76 | 73 ± 1 | 1970 ± 118 |
| PDCHDMA/HDDMA 75/25 wt % | 9.2 ± 0.34 | 61 ± 0.33 | | 4.59 ± 0.17 | | |
| DPHDMA/HDDMA 80/20 wt % | 2.58 ± 0.06 | 81 ± 0.31 | | 5.8 ± 0.31 | 68 ± 5 | 2000 ± 323 |
| DPHDMA/HDDMA 75/25 wt % | 1.64 ± 0.02 | 73 ± 1.11 | | 6.1 ± 0.14 | 74 ± 2 | 1469 ± 162 |
| DPHDMA/HDDMA 70/30 wt % | 0.97 ± 0.02 | 71 ± 1.08 | | 6.5 ± 0.30 | 79 ± 4 | 1651 ± 33 |
| DPHDMA/HDDMA 68/32 wt % | 0.79 ± 0.04 | 79 ± 1.15 | | 6.4 ± 0.23 | 81 ± 4 | 1702 ± 99 |
| TBPPHDMA/DADMA 80/20 wt % | 1.96 ± 0.02 | 78 ± 0.7 | 1.5131 | 4.19 ± 0.60 | 62 ± 4 | 1349 ± 187 |
| TBPPHDMA/DADMA 75/25 wt % | 25.5 ± 0.38 | 80 ± 0.7 | 1.5104 | 3.83 ± 0.20 | 56 ± 4 | 1059 ± 87 |
| TBPPHDMA/DADMA 70/30 wt % | 18.4 ± 0.11 | 86 ± 0.56 | 1.5082 | 3.89 ± 0.09 | 52 ± 2 | 984 ± 17 |
| TBPPHDMA/DDCDMA 70/30 wt % | 20.14 ± 0.04 | 83 ± 0.52 | 1.5057 | 4.14 ± 0.26 | 64 ± 3 | 1204 ± 71 |
| TBPPHDMA/DDCDMA 75/25 wt % | 2.60 ± 0.02(50° C.) | 73 ± 0.60 | 1.5119 | 3.36 ± 0.16 | 69 ± 2 | 1338 ± 67 | nD = Refractive index at 20° C.
FS = Flexural strength

TABLE 3

| Composition | Consistency | Depth of Cure (mm) | Conversion (%) | Volume Shrinkage (%) | FS (MPa) | Modulus (MPa) | DTS (MPa) | CS (MPa) |
|---|---|---|---|---|---|---|---|---|
| TBPPHDMA/HDDMA 80/20 wt % | 17 × 17 | 2.204 | 64.0 ± 0.5 | 2.50 ± 0.15 | 105 ± 4 | 7443 ± 41 | 37 ± 2 | 170 ± 13 |
| TBPPHDMA/HDDMA 75/25 wt % | 17 × 17 | 2.469 | 65 ± 0.8 | 1.74 ± 0.27 | 105 ± 7 | 7983 ± 350 | 42 ± 1 | 197 ± 14 |
| TBPPHDMA/HDDMA 80/20 wt % | 24 × 24 | 2.391 | 64 ± 0.35 | 3.36 ± 0.16 | 65 ± 4 | 5419 ± 247 | 30 ± 6 | 224 ± 15 |
| TBPPHDMA/HDDMA 75/25 wt % | 24 × 24 | 2.349 | 65 ± 0.08 | | 90 ± 7 | 6545 ± 545 | 35 ± 6 | 211 ± 14 |
| TBPPHDMA/HDDMA 70/30 wt % | 17 × 17 | 2.457 | 68 ± 0.38 | 2.78 ± 0.51 | 91 ± 9 | 7784 ± 453 | 39 ± 1 | 155 ± 14 |

TABLE 3-continued

| Composition | Consistency | Depth of Cure (mm) | Conversion (%) | Volume Shrinkage (%) | FS (MPa) | Modulus (MPa) | DTS (MPa) | CS (MPa) |
|---|---|---|---|---|---|---|---|---|
| TBPPHDMA/HDDMA 80/20 wt % | 26 × 26 | 2.475 | 56 ± 0.34 | 1.90 ± 0.23 | 79 ± 6 | 5796 ± 169 | 34 ± 2 | 163 ± 18 |
| TBPPHDMA/HDDMA 75/25 wt % | 26 × 26 | 2.383 | 57 ± 0.83 | 2.07 ± 0.05 | 87 ± 2 | 6017 ± 435 | 37 ± 3 | 150 ± 35 |
| TBPPHDMA/HDDMA 70/30 wt % | 26 × 26 | 2.396 | 60 ± 0.26 | 2.35 ± 0.19 | 100 ± 3 | 8007 ± 395 | 31 ± 3 | 166 ± 12 |
| TBPPHDMA/HDDMA 80/20 wt % | 22 × 22 | 2.443 | 66 ± 0.87 | 2.68 ± 0.29 | 78 ± 3 | 6134 ± 560 | 30 ± 4 | 225 ± 14 |
| TBPPHDMA/HDDMA 75/25 wt % | 22 × 22 | 2.458 | 65 ± 0.73 | 2.66 ± 0.23 | 80 ± 2 | 6835 ± 118 | 33 ± 3 | 229 ± 16 |
| TBPPHDMA/HDDMA 70/30 wt % | 22 × 22 | 2.483 | 64 ± 0.99 | 2.53 ± 0.20 | 70 ± 3 | 4409 ± 420 | 35 ± 3 | 176 ± 21 |
| TBPPHDMA/HDDMA 75/25 wt % | 17 × 17 | 3.606 | 66 ± 0.35 | 2.04 ± 0.44 | 83 ± 2 | 6492 ± 561 | 39 ± 3 | 162 ± 23 |
| TBPPHDMA/HDDMA 70/30 wt % | 26 × 26 | 3.033 | 62 ± 0.73 | 2.62 ± 0.41 | 78 ± 7 | 6766 ± 263 | 30 ± 2 | 262 ± 25 |
| TBPPHDMA/HDDMA 75/25 wt % | 22 × 22 | 3.474 | 70 ± 0.17 | 1.75 ± 0.36 | 84 ± 4 | 7173 ± 415 | 36 ± 3 | 211 ± 12 |

TABLE 4

| Composition | Consistency | Depth of Cure (mm) | Conversion (%) | Volume Shrinkage (%) | Flexural Strength (MPa) | Modulus (MPa) | DTS (MPa) | Compressive Stress (MPa) |
|---|---|---|---|---|---|---|---|---|
| TBPPHDMA/HDDMA 80/20 wt % | 24 × 24 | 2.391 | 64 ± 0.35 | 3.36 ± 0.16 | 65 ± 4 | 5419 ± 247 | 30 ± 6 | 224 ± 15 |
| TBPPHDMA/HDDMA 75/25 wt % | 24 × 24 | 2.349 | 65 ± 0.08 |  | 90 ± 7 | 6545 ± 545 | 35 ± 6 | 211 ± 14 |
| TBPPHDMA/HDDMA 80/20 wt % | 26 × 26 | 2.475 | 56 ± 0.34 | 1.90 ± 0.23 | 79 ± 6 | 5796 ± 169 | 34 ± 2 | 163 ± 18 |
| TBPPHDMA/HDDMA 75/25 wt % | 26 × 26 | 2.383 | 57 ± 0.83 | 2.07 ± 0.05 | 87 ± 2 | 6017 ± 435 | 37 ± 3 | 150 ± 35 |
| TBPPHDMA/HDDMA 70/30 wt % | 26 × 26 | 2.396 | 60 ± 0.26 | 2.35 ± 0.19 | 100 ± 3 | 8007 ± 395 | 31 ± 3 | 166 ± 12 |
| TBPPHDMA/HDDMA 80/20 wt % | 22 × 22 | 2.443 | 66 ± 0.87 | 2.68 ± 0.29 | 78 ± 3 | 6134 ± 560 | 30 ± 4 | 225 ± 14 |
| TBPPHDMA/HDDMA 75/25 wt % | 22 × 22 | 2.458 | 65 ± 0.73 | 2.66 ± 0.23 | 80 ± 2 | 6835 ± 118 | 33 ± 3 | 229 ± 16 |
| TBPPHDMA/HDDMA 70/30 wt % | 26 × 26 | 3.033 | 62 ± 0.73 | 2.62 ± 0.41 | 78 ± 7 | 6766 ± 263 | 30 ± 2 | 262 ± 25 |
| TBPPHDMA/HDDMA 75/25 wt % | 22 × 22 | 3.474 | 70 ± 0.17 | 1.75 ± 0.36 | 84 ± 4 | 7173 ± 415 | 36 ± 3 | 211 ± 12 |
| TBPPHDMA/HDDMA 75/25 wt % | 20 × 20 |  |  |  | 91.1 ± 0.5 | 8498 ± 435 | 39 ± 3 | 243 ± 8 |

TABLE 5

| Composition | Consistency | Depth of Cure (mm) | Conversion (%) | Volume Shrinkage (%) | FS (MPa) | Modulus (MPa) | DTS (MPa) | CS (MPa) |
|---|---|---|---|---|---|---|---|---|
| TBPPHDMA/DDCDMA 70/30 wt % | 24 × 24 | 2.278 | 65 ± 0.56 |  | 86 ± 5 | 4971 ± 449 | 34 ± 3 | 114 ± 14 |
| TBPPHDMA/DDCDMA 75/25 wt % | 24 × 24 | 2.299 | 62 ± 1.05 |  | 88 ± 5 | 5569 ± 273 | 35 ± 3 | 174 ± 17 |
| TBPPHDMA/DDCDMA 70/30 wt % | 22 × 22 | 2.483 | 64 ± 0.99 | 2.53 ± 0.20 | 70 ± 3 | 4409 ± 420 | 35 ± 3 | 176 ± 21 |
| TBPPHDMA/DDCDMA/UDMA 60/25/15 wt % | 22 × 22 | 2.382 | 65 ± 0.81 | 1.63 ± 0.31 | 68 ± 8 | 4678 ± 483 | 33 ± 2 | 157 ± 13 |

TABLE 6

Results for Pit & Fissure sealants formulations using the monomers of the present invention compared to a commercial product

| Compound | Conversion (%) | Volume Shrinkage (%) | Flexural Strength (Mpa) | Modulus (Mpa) |
|---|---|---|---|---|
| Delton P&F Sealant | 85 ± 2 a | 8.60 ± 0.75 b | 60 ± 8 b | 2060 ± 319 a |
| Composition 31 | 77 ± 1 b | 4.89 ± 0.26 a | 66 ± 3 b | 1281 ± 137 b |
| Composition 32 | 76 ± 1 b | 5.05 ± 0.11 a | 62 ± 3 b | 1295 ± 75 b |
| Composition 33 | 76 ± 1 b | 4.79 ± 0.36 a | 80 ± 7 a | 1826 ± 193 a |
| Composition 35 | 72 ± 1 c | 4.96 ± 0.65 a | 59 ± 4 b | 1173 ± 145 b |
| Composition 36 | 68 ± 1 d | 5.50 ± 0.57 a | 75 ± 6 a | 1713 ± 55 a |
| Composition 37 | 72 ± 1 c | 4.64 ± 0.26 a | 78 ± 7 a | 1866 ± 220 a |

What is claimed:

1. A compound of formula (I):

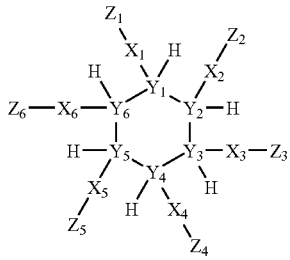

wherein:
the ring structure of formula (I) is saturated or contains up to three unsaturations;

Y1-Y6, each independent from each other, is selected from the group consisting of: C, O, N, and S, wherein at least one of Y1-Y6 is O, N, or S, with the proviso that at least two of Y1-Y6 is C, and wherein:

(i) when any one of Y1-Y6 is O, S, or an unsaturated nitrogen, then the corresponding H, X1-X6 and Z1-Z6 are absent, and ii) when any one of Y1-Y6 is a saturated nitrogen or an unsaturated carbon, then the corresponding H is absent;

X1-X6, each independent from each other, is a direct bond, or is selected from the group consisting of: =O, =S, and Rx, wherein Rx is a C1-C10 group optionally having at least one unsaturation, branch and/or cycle, which is substituted up to 4 times or unsubstituted, and which may be interrupted by at least one O or S, wherein the substituents are each independently selected from the group consisting of —OH, —OR, =O, =S, —O2CR, —SH, —SR, —SOCR, —NH2, —NHR, —N(R)2, —NHCOR, —NRCOR, 1, —Br, —Cl, —F, —CN, —CO2H, —CO2R, —CHO, —COR, —CONH2, —CONHR, —CON(R)2, —COSH, —COSR, —NO2, —SO3H, —SOR, and —SO2R, wherein R is a linear, branched or cyclic alkyl of one to ten carbon atoms, Z1-Z6, each independent from each other, is selected from the group consisting of:

(a) H;

(b) a radical of formula (II):

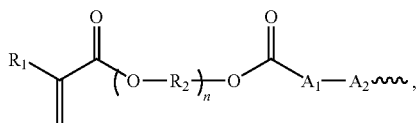

wherein:
R1 is selected from the group consisting of: H and Rx, as described above,
R2 is Rx, as described above;
n is an integer from 1 to 10,
A1 is a direct bond or Rx, as described above; and
A2 is selected from the group consisting of O and NH;

(c) a radical of formula (V)

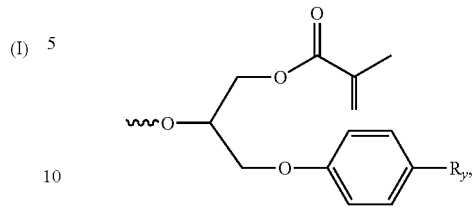

wherein Ry is selected from the group consisting of H, CH3, CH2CH3, C(CH3)3, OH, COOH, anhydride, O=P(OH)2, and =P(CH2)m(OH)2, wherein m=1 to 4; and (d) a radical of formula (VI):

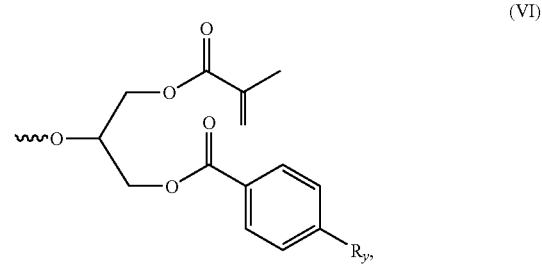

wherein Ry is as described above;
with the proviso that at least two of Z1-Z6 is independently a radical of formula, (V) or (VI);
and wherein when any one of X1-X6 is H, =O, or =S, then the respective Z1-Z6 is absent.

2. The compound of claim 1, wherein at least two of Y1-Y6 are selected from the group consisting of: C, O, N, and S.

3. The compound of claim 1, wherein at least one of X1-X6 is =O or =S, Rx, or a C6 group.

4. The compound of claim 1, wherein one or more of Z1-Z6 is the following:

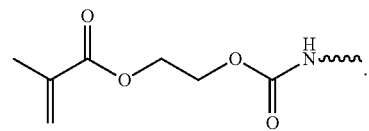

5. The compound of claim 1, wherein in formula (II), R1 is a CH3, R2 is a C2 alkyl, n is 1, A1 is a direct bond, and A2 is NH.

6. A process of producing the compound of formula (I) in claim 1, comprising reacting:

(1) a compound of formula (Is):

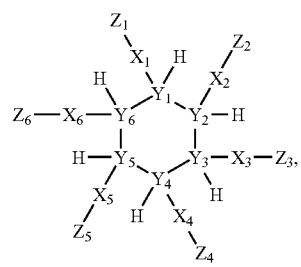

wherein Y1-Y6 are as defined for formula (I);

wherein X1-X6 are as defined for formula (I); and and wherein Z7-Z12, independent from each other, are selected from the group consisting of H, —N=C=O, and —COOH, with the proviso that at least one of Z7-Z12 is —N=C=O or —COOH; and wherein when any one of X1-X6 is H, =O, or =S, then the respective Z7-Z12 is absent; with (2) a compound selected from the group consisting of:

(a) a compound of formula (IV)

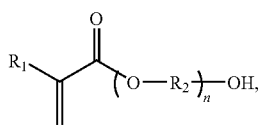

wherein R1, R2 and n are as defined for formula (II), b) a compound of formula (Vs):

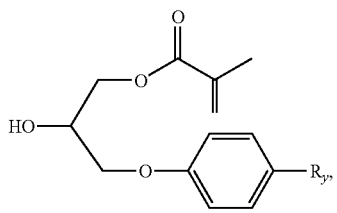

wherein Ry is as defined in claim 1; and c) a compound of formula (VIs):

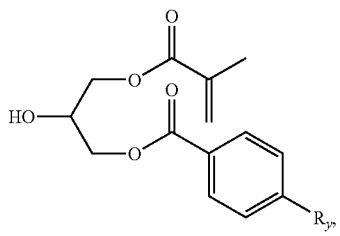

wherein Ry is as defined in claim 1.

7. The process of claim 6, wherein the compound of formula (IV) is hydroxyethyl methacrylate (HEMA):

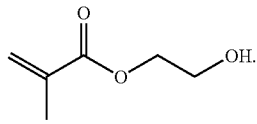

8. The process of claim 6, further comprising the step of providing one or more catalysts to the reaction.

9. The process of claim 8, wherein the catalyst is selected from the group consisting of: tertiary amines, organometallic compounds selected from the group consisting of dibutyl tin dilaurate (DBTDL), dioctyl tin dilaurate (DOTDL), and zirconium acetylacetonate.

10. The process of claim 6, further comprising the step of providing one or more stabilizers to the reaction.

11. The process of claim 10, wherein the stabilizer is selected from the group consisting of: hydroquinone monomethylether (MEHQ), a p-benzoquinone, 2,6-di-tert-butyl-p-cresol (BHT), and a p-butyl-hydroxytoluene.

12. The process of claim 6, wherein the process occurs at a temperature of about 20 to 50° C.

13. The process of claim 6, wherein the reaction with hydroxyethyl methacrylate occurs over a time period of between about 18 to about 48 hours.

14. A composition comprising the compound of formula (I) of claim 1.

15. The composition of claim 14, wherein the composition further comprises one or more monomers selected from the group consisting of: EBPADMA, UDMA, DDCDMA, DAO-HDMA, 1,6 hexanediol dimethacrylate (HDDMA), 1,4 butanediol dimethacrylate, 1,9 nonanediol dimethacrylate, undecyl methacrylate, lauryl methacrylate, norbornyl methacrylate, isobornyl methacrylate, and n-octyl methacrylate.

16. The composition of claim 14, wherein the composition further comprises one or more filler materials selected from the group consisting of: silanized inorganic compounds, silica, silicate glass, quartz, barium silicate, strontium silicate, barium borosilicate, strontium borosilicate, borosilicate, alumina, zirconia, tin oxide, ytterbium fluoride, and pigments.

17. The composition of claim 14, wherein the composition further comprises one of more filler materials, wherein the particle sizes of the one or more filler materials are between about 0.001 to about 5.0 micrometers.

18. A method of treating a patient in need of application of a dental treatment, comprising providing a polymer to said patient, wherein said polymer is prepared from a compound of formula (I) according to claim 1.

19. The method of claim 18, wherein the application of a dental treatment is selected from the group consisting of: dental adhesives; permanent and temporary dental resin cements; light cure and chemical cure dental nanohybrid, microhybrid, and hybrid composites; dental nanohybrid and microhybrid flowable composites; temporary filling material; core build up material; and pit and fissure sealants.

20. A compound of formula (III):

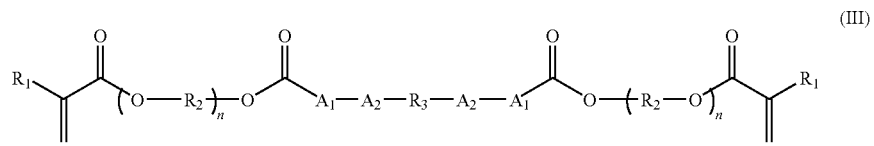

R1 is selected from the group consisting of: H and Rx, wherein Rx is a C1-C10 group optionally having at least one unsaturation, branch or cycle, which is substituted up to 4 times or unsubstituted and which may be interrupted by at least one O or S, wherein the substituents are each independently selected from the group consisting of —OH, —OR, =O, =S, —O2CR, —SH, —SR, —SOCR, —NH2, —NHR, —N(R)$_2$, —NHCOR, —NRCOR, —I, —Br, —Cl, —F, —ON, —CO2H, —CO2R, —CHO, —COR, —CONH2, —CONHR, —CON(R)2, —COSH, —COSR, —NO2, —SO3H, —SOR, and —SO2R, wherein R is a linear, branched or cyclic alkyl of one to ten carbon atoms, and wherein each R1 in formula (III) may be the same or different;

R2 is Rx, as defined above, or a C9-C25 group optionally having at least one unsaturation, branch or cycle, which is substituted up to 4 times or unsubstituted and which may be interrupted by at least one O or S, wherein the substituents are each independently selected from the group consisting of —OH, —OR, =O, =S, —O2CR, —SH, —SR, —SOCR, —NH2, —NHR, —N(R)$_2$, —NHCOR, —NRCOR, —I, —Br, —Cl, —F, —ON, —CO2H, —CO2R, —CHO, —COR, —CONH2, —CONHR, —CON(R)2, —COSH, —COSR, —NO2, —SO3H, —SOR, and —SO2R, wherein R is a linear, branched or cyclic alkyl of one to ten carbon atoms, wherein each R2 in formula (III) may be the same or different, and wherein at least one R2 group comprises an aromatic group;

R3 is a C6-C50 group optionally having at least one unsaturation, branch or cycle, which is substituted up to 4 times or unsubstituted and which may be interrupted by at least one O or S, wherein the substituents are each independently selected from the group consisting of —OH, —OR, =O, =S, —O2CR, —SH, —SR, —SOCR, —NH2, —NHR, —N(R)2, —NHCOR, —NRCOR, —I, —Br, —Cl, —F, —ON, —CO2H, —CO2R, —CHO, —COR, —CONH2, CONHR, —CON(R)2, —COSH, —COSR, —NO2, —SO3H, —SOR, and —SO2R, wherein R is a linear, branched or cyclic alkyl of one to ten carbon atoms n is an integer from 1 to 10;

A1 is a direct bond or Rx, as described above; and

A2 is selected from the group consisting of O and NH, wherein the compound of formula (III) is selected from the group consisting of

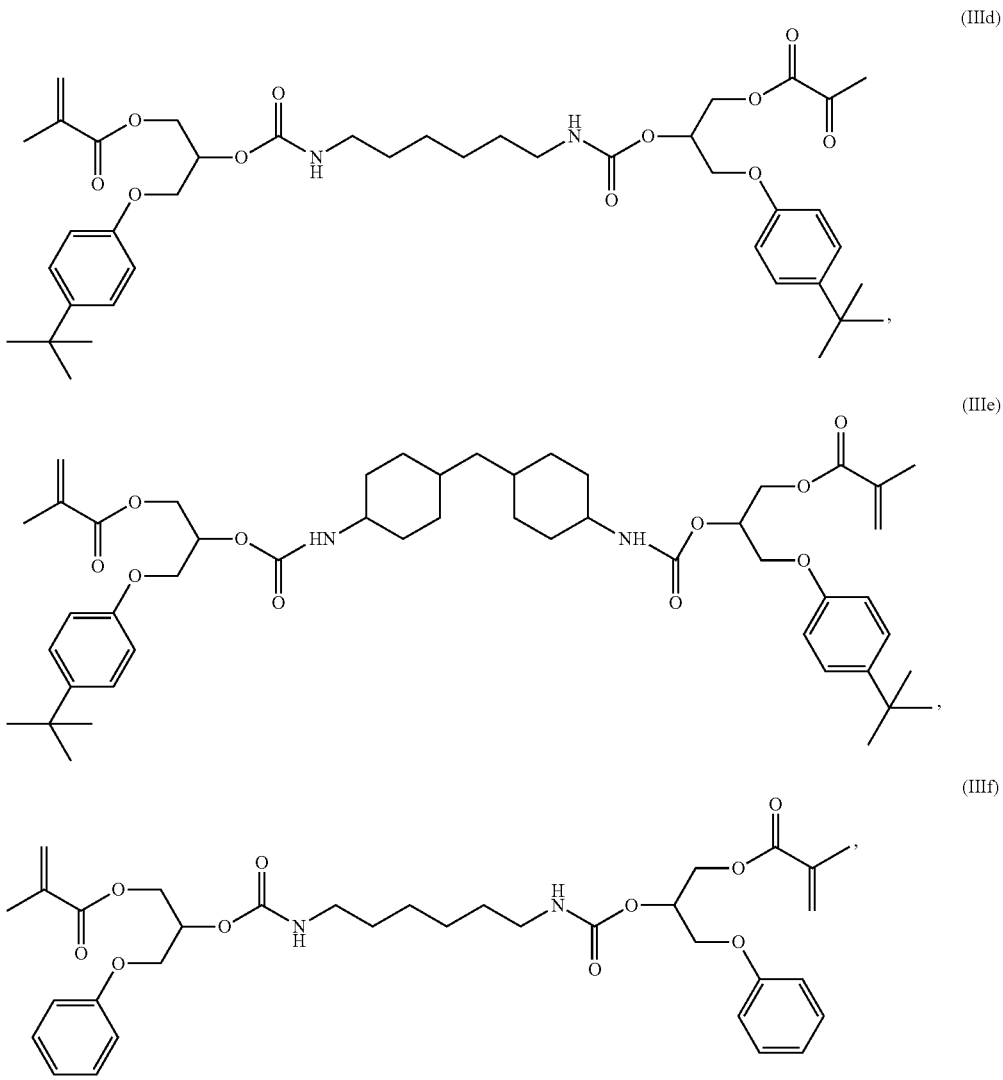

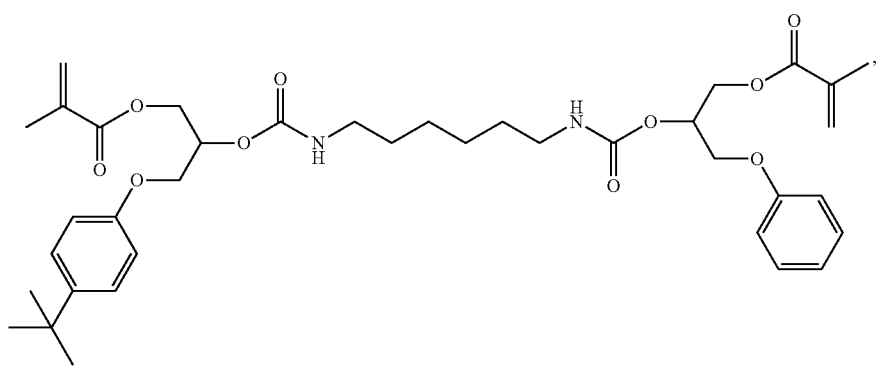
(IIIg)
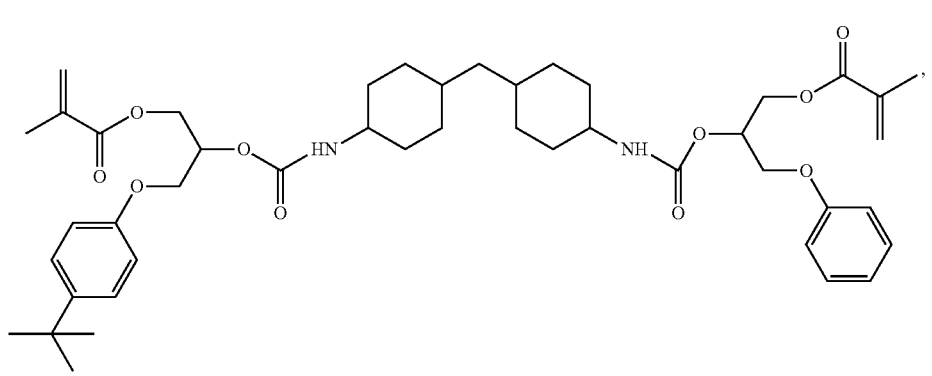
(IIIh)
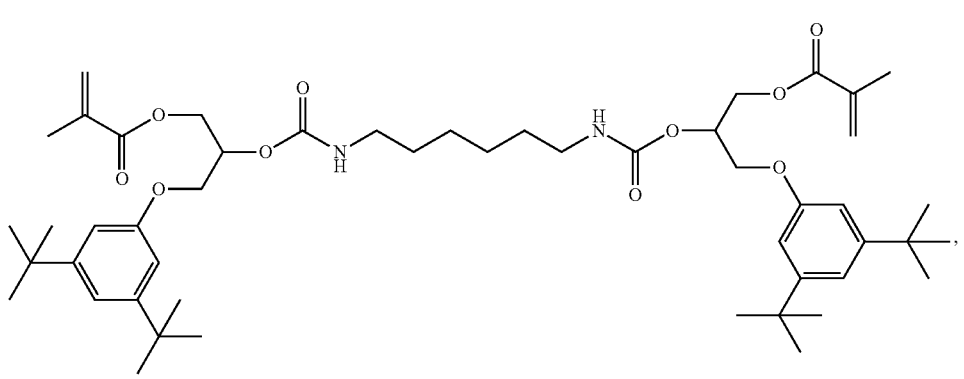
(IIIi)
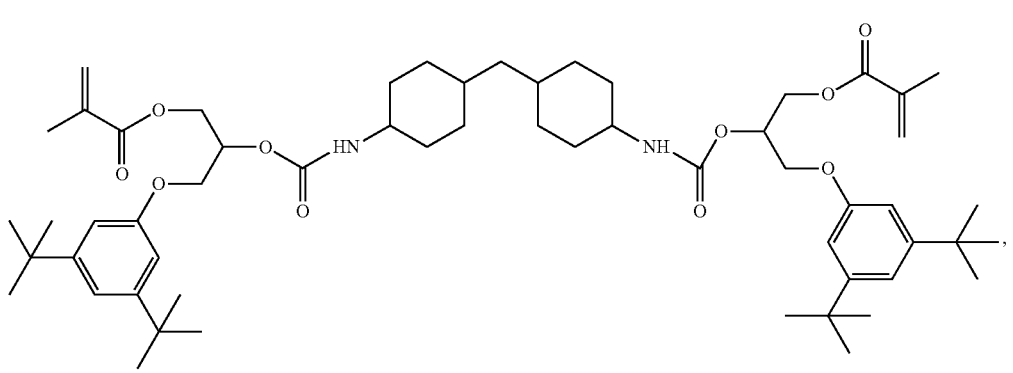
(IIIj)

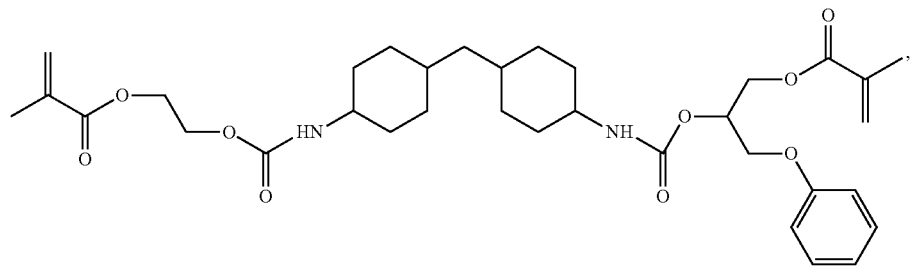

(IIIk)

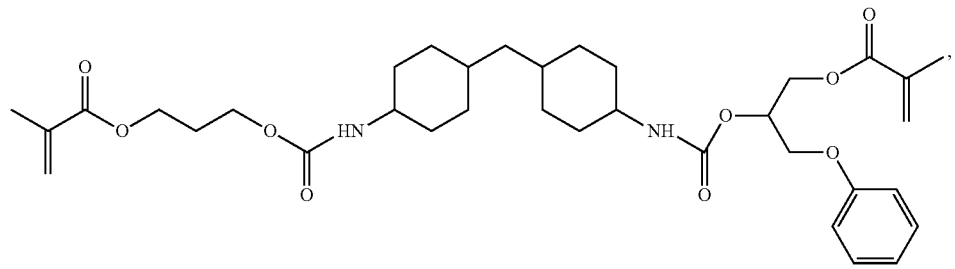

(IIIL)

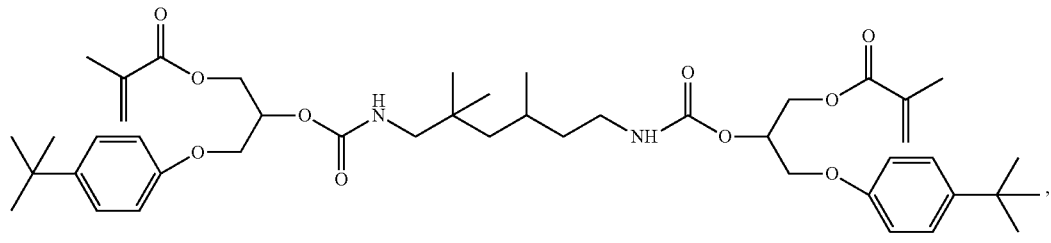

(IIIm)

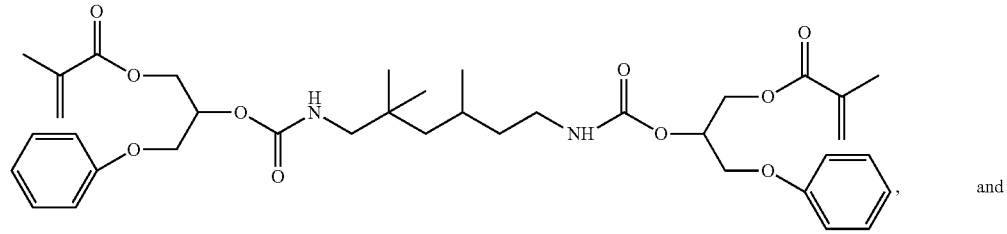

(IIIn)

and

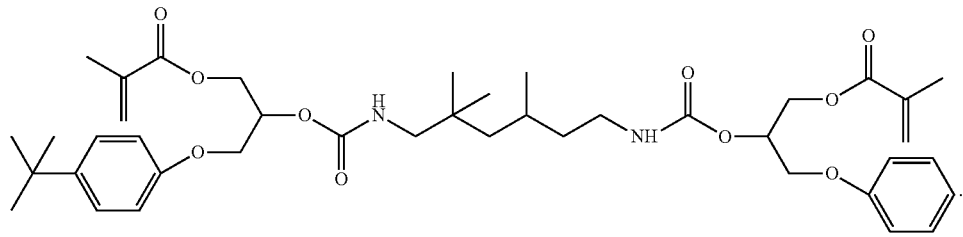

(IIIo)

21. A composition comprising the compound of formula (III) of claim 7.

22. The composition of claim 21, wherein the composition further comprises one or more monomers selected from the group consisting of: EBPADMA, UDMA, DDCDMA, DAO-HDMA, 1,6 hexanediol dimethacrylate (HDDMA), 1,4 butanediol dimethacrylate, 1,9 nonanediol dimethacrylate, undecyl methacrylate, lauryl methacrylate, norbornyl methacrylate, isobornyl methacrylate, and n-octyl methacrylate.

23. The composition of claim 21, wherein the composition further comprises one or more filler materials selected from the group consisting of: silanized inorganic compounds, silica, silicate glass, quartz, barium silicate, strontium silicate, barium borosilicate, strontium borosilicate, borosilicate, alumina, zirconia, tin oxide, ytterbium fluoride, and pigments.

24. The composition of claim 21, wherein the composition further comprises one of more filler materials, wherein the particle sizes of the one or more filler materials are between about 0.001 to about 5.0 micrometers.

25. A method of treating a patient in need of application of a dental treatment, comprising providing a polymer to said patient, wherein said polymer is prepared from a compound of formula (III) according to claim 20.

26. The method of claim 25, wherein the application of a dental treatment is selected from the group consisting of:

dental adhesives; permanent and temporary dental resin cements; light cure and chemical cure dental nanohybrid, microhybrid, and hybrid composites; dental nanohybrid and microhybrid flowable composites; temporary filling material; core build up material; and pit and fissure sealants.

* * * * *